(12) United States Patent
Van Snick et al.

(10) Patent No.: US 10,035,851 B2
(45) Date of Patent: Jul. 31, 2018

(54) TGF-β1 SPECIFIC ANTIBODIES AND METHODS AND USES THEREOF

(71) Applicants: Jacques Van Snick, Brussels (BE); Catherine Uyttenhove, Brussels (BE); Thierry Boon, Brussels (BE)

(72) Inventors: Jacques Van Snick, Brussels (BE); Catherine Uyttenhove, Brussels (BE); Thierry Boon, Brussels (BE)

(73) Assignee: LUDWIG INSTITUTE FOR CANCER RESEARCH LTD., New York, NY (US)

( * ) Notice: Subject to any disclaimer, the term of this patent is extended or adjusted under 35 U.S.C. 154(b) by 0 days.

(21) Appl. No.: 15/341,077

(22) Filed: Nov. 2, 2016

(65) Prior Publication Data

US 2017/0137507 A1 May 18, 2017

Related U.S. Application Data

(62) Division of application No. 14/383,602, filed as application No. PCT/US2013/029334 on Mar. 6, 2013, now Pat. No. 9,518,112.

(60) Provisional application No. 61/608,393, filed on Mar. 8, 2012.

(51) Int. Cl.
C07K 16/22 (2006.01)
A61K 39/00 (2006.01)

(52) U.S. Cl.
CPC ........ *C07K 16/22* (2013.01); *A61K 2039/505* (2013.01); *C07K 2317/33* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| 5,571,714 | A  | 11/1996 | Dasch et al. |
| 6,492,497 | B1 | 12/2002 | Thompson et al. |
| 2009/0202526 | A1 | 8/2009 | Pons |
| 2009/0285810 | A1 | 11/2009 | Adams et al. |
| 2010/0196359 | A1 | 8/2010 | Kato et al. |
| 2010/0291545 | A1 | 11/2010 | Wakita et al. |
| 2012/0141465 | A1 | 6/2012 | Croft et al. |
| 2012/0328660 | A1 | 12/2012 | Tsuji et al. |

FOREIGN PATENT DOCUMENTS

| WO | 00020581 | 4/2000 |
| WO | 00066631 | 11/2000 |
| WO | 05097832 | 10/2005 |
| WO | 06086469 | 8/2006 |
| WO | 06116002 | 11/2006 |
| WO | 07076391 | 7/2007 |

OTHER PUBLICATIONS

Ahmadzadeh, M et al (2005) TGF-beta 1 attenuates the acquisition and expression of effector function by tumor antigen-specific human memory CD8 T cells J Immunol 174(9):5215-5223.
Arteaga, Carlos L et al (1993) Transforming growth factor beta 1 can induce estrogen-independent tumorigenicity of human breast cancer cells in athymic mice Cell Growth Diff 4(3):193-201.
Arteaga, CL et al (1993) Anti-transforming growth factor (TGF)-beta antibodies inhibit breast cancer cell tumorigenicity and increase mouse spleen natural killer cell activity. Implications for a possible role of tumor cell/host TGF-beta Interactions in human breast cancer progression J Clin Invest 92(6):2569-2576.
Arteaga, CL (2006) Inhibition of TGFbeta signaling in cancer therapy Curr Opin Genet Dev 16(1):30-37.
Banovic, T et al (2005) TGF-beta in allogeneic stem cell transplantation: friend or foe? Blood 106(6):2206-2214.
Biswas S et al (2007) Inhibition of TGF-beta with neutralizing antibodies prevents radiation-induced acceleration of metastatic cancer progression J Clin Invest 117(5):1305-1313.
Bollard, CM et al (2002) Adapting a transforming growth factor beta-related tumor protection strategy to enhance antitumor immunity Blood 99(9):3179-3187.
Broderick, L et al (2006) Membrane-associated TGF-beta1 inhibits human memory T cell signaling in malignant and nonmalignant inflammatory microenvironments J Immunol 177(5):3082-3088.
Dasch Jr et al (1989) Monoclonal antibodies recognizing transforming growth factor-beta Bioactivity neutralization and transforming growth factor beta 2 affinity purification J Immunol 142(5):1536-1541.
Derynck R et al (1986) The murine transforming growth factor-beta precursor. J Biol Chem 261(10):4377-4379.
Di Bari, MG et al (2009) TGF-beta modulates the functionality of tumor-infiltrating CD8-+ T cells through effects on TCR signaling and Spred1 expression Cancer Immunol Immunother 58(11):1809-1818.
Fong, L et al (2008) Anti-cytotoxic T-lymphocyte antigen-4 antibody: the first in an emerging class of Immunomodulatory antibodies for cancer treatment J Clin Oncol 26(32):5275-5283.

(Continued)

*Primary Examiner* — Brian Gangle
*Assistant Examiner* — Andrea K McCollum
(74) *Attorney, Agent, or Firm* — Klauber & Jackson LLC

(57) ABSTRACT

Specific binding members, particularly antibodies and fragments thereof, which bind to transforming growth factor beta 1 (TGF-β1) are provided, particularly recognizing human and mouse TGF-β1 and not recognizing or binding TGF-β2 or TGF-β3. Particular antibodies are provided which specifically recognize and neutralize TGF-β1. These antibodies are useful in the diagnosis and treatment of conditions associated with activated or elevated TGF-β1, including cancer, and for modulating immune cells and immune response, including immune response to cancer or cancer antigens. The anti-TGF-β1 antibodies, variable regions or CDR domain sequences thereof, and fragments thereof may also be used in therapy in combination with chemotherapeutics, immune modulators, or anti-cancer agents and/or with other antibodies or fragments thereof. Antibodies of this type are exemplified by the novel antibodies hereof, including antibody 13A1, whose sequences are provided herein.

12 Claims, 7 Drawing Sheets

(56) References Cited

OTHER PUBLICATIONS

Garrison, K et al (2012) the small molecule TGF-β signaling inhibitor SM16 synergizes with agonistic OX40 antibody to suppress established mammary tumors and reduce spontaneous metastasis.Cancer Immunol Immunothe 61 (4):511-521.

Ito, N et al (1995) Positive correlation of plasma transforming growth factor-beta 1 levels with tumor vascularity in hepatocellular carcinoma Cancer Lett 89(1):45-48.

Liu, VC et al (2007) Tumor evasion of the immune system by converting CD4+CD25- T cells into CD4+CD25+T regulatory cells: role of tumor-derived TGF-beta J Immunol 178(5): 2883-2892.

Muraoka-Cook, RS et al (2004) Conditional overexpression of active transforming growth factor beta1 in vivo accelerates metastases of transgenic mammary tumors Cancer Res 64(24):9002-9011.

Nabel, EG et al (1993) Direct transfer of transforming growth factor beta 1 gene into arteries stimulates fibrocellular hyperplasia Proc Natl Acad Sci 90(22):10759-10763.

Nam, JS et al (2008) An anti-transforming growth factor beta antibody suppresses metastasis via cooperative effects on multiple cell compartments Cancer Res 68(10):3835-3843.

Pasquale, LR et al (1993) Immunolocalization of TGF-beta 1, TGF-beta 2, and TGF-beta 3 in the anterior segment of hte human eye Invest Ophthalmol Vis Sci 34(1):23-30.

Sabbatini, P et al (2012) Phase I trial of overlapping long peptides from a tumor self-antigen and poly-ICLC shows rapid induction of integrated immune response in ovarian cancer patients Clin Cancer Res 18(23):6497-6508.

Sato, E et al (2005) Intraepithelial CD8+ tumor-infiltrating lymphocytes and a high CD8+/regulatory T cell ratio are associated with favorable prognosis in ovarian cancer Proc Natl Acad Sci USA 102(51):18538-18543.

Shah, M et al (1995) Neutralisation of TGF-beta 1 and TGF-beta 2 or exogenous addition of TGF-beta 3 to cutaneous rat wounds reduces scarring J Cell Sci 108(Pt 3):985-1002.

Shah, AH et al (2002) Reconstitution of lethally irradiated adult mice with dominant negative TGF-beta type II receptor-transduced bone marrow leads to myeloid expansion and inflammatory disease J Immunol 169(7):3485-3491.

Shariat, Shahrakh F et al (2001) Preoperative plasma levels of transforming growth factor beta(1) (TGF-beta(1)) strongly predict progression in patients undergoing radical prostatectomy J Clin Oncol 19(11):2856-2864.

Shariat, SF et al (2001) Preoperative plasma levels of transforming growth factor beta(1) strongly predict clinical outcome in patients with bladder carcinoma Cancer 92(12):2985-2992.

Siegel, Peter M et al (2003) Cytostatic and apoptotic actions of TGF-beta in homeostasis and cancer Nat Rev Cancer 3(11):807-821.

Siegel, PM et al (2003) Transforming growth factor beta signaling impairs Neu-induced mammary tumorigenesis while promoting pulmonary metastasis Proc Natl Acad Sci USA 100(14):8430-8435.

Takaku, S et al (2010) Blockade of TGF-beta enhances tumor vaccine efficacy mediated by CD8(+) T cells Int J Cancer 126(7):1666-1674.

Teicher, Beverly A et al (1997) Prostate carcinoma response to cytotoxic therapy: in vivo resistance In Vivo 11(6):453-461.

Teicher, BA et al (1997) Transforming growth factor-beta 1 overexpression produces drug resistance in vivo: reversal by decorin In Vivo 11(6):463-472.

Terabe. M et al (2003) Transforming growth factor-beta production and myeloid cells are an effector mechanism through which CD1d-restricted T cells block cytotoxic T lymphocyte-mediated tumor immunosurveillance: abrogation prevents tumor recurrence J Exp Med 198(11):1741-1752.

Terabe, M et al (2009) Synergistic enhancement of CD8+ T cell-mediated tumor vaccine efficacy by an anti-transforming growth factor-beta monoclonal antibody Clin Cancer Res 15(21):6560-6569.

Tsushima, H et al (2001) Circulating transforming growth factor beta 1 as a predictor of liver metastasis after resection in colorectal cancer Clin Cancer Res 7(5):1258-1262.

Wojtowicz-Praga, S (2003) Reversal of tumor-induced immunosuppression by TGF-beta inhibitors Invest New Drugs 21(1):21-32.

Yang, L et al (2010) Gr-1+CD11b+ myeloid-derived suppressor cells: formidable partners in tumor metastasis J Bone Miner Res 25(8):1701-1706.

Zhang, Q et al (2005) Adoptive transfer of tumor-reactive transforming growth factor-beta-insensitive CD8+ T cells: eradication of autologous mouse prostate cancer Cancer Res 65(5):1761-1769.

Zhang, Q et al (2006) Blockade of transforming growth factor-{beta} signaling in tumor-reactive CD8(+) T cells activates the antitumor immune response cycle Mol Cancer Ther 5(7):1733-1743.

Fig. 1A

13A1 HEAVY CHAIN
Amino Acid Sequence
LARPGASVKMSCKTSGYTFTNYWMHWVRQRPGQGLEWIGTIYPGNS
DTNYNQKFKDKAKLTAVTSATTAYMELSSLTNEDSAVYFCTREDSRSL
YYNGWDYFDYWGQGTTLTVSS 13A1 LIGHT CHAIN
Amino Acid Sequence
LTQSPASLAVSLGQRATISCRASESVDNYGISFLNWFQQKPGQPPKLLI
YAASNQGSGVPARFSGSGSGTDFSLNIHPMEEDDTGMYFCQQSKEVPR
TFGGGTKLEII

Fig. 1B

CDRs

| | |
|---|---|
| CDRH1 | GYTFTNYWMH or GYTFTNYW |
| CDRH2 | TIYPGNSDTN or IYPGNSDT |
| CDRH3 | EDSRSLYYNGWDYFDY |
| | |
| CDRL1 | ESVDNYGISF |
| CDRL2 | YAAS |
| CDRL3 | QQSKEVPRT |

SEQUENCE LISTING

```
<160> NUMBER OF SEQ ID NOS: 12

<210> SEQ ID NO 1
<211> LENGTH: 115
<212> TYPE: PRT
<213> ORGANISM: Mus musculus

<400> SEQUENCE: 1

Leu Ala Arg Pro Gly Ala Ser Val Lys Met Ser Cys Lys Thr Ser Gly
1               5                   10                  15

Tyr Thr Phe Thr Asn Tyr Trp Met His Trp Val Arg Gln Arg Pro Gly
                20                  25                  30

Gln Gly Leu Glu Trp Ile Gly Thr Ile Tyr Pro Gly Asn Ser Asp Thr
            35                  40                  45

Asn Tyr Asn Gln Lys Phe Lys Asp Lys Ala Lys Leu Thr Ala Val Thr
        50                  55                  60

Ser Ala Thr Thr Ala Tyr Met Glu Leu Ser Ser Leu Thr Asn Glu Asp
65                  70                  75                  80

Ser Ala Val Tyr Phe Cys Thr Arg Glu Asp Ser Arg Ser Leu Tyr Tyr
                85                  90                  95

Asn Gly Trp Asp Tyr Phe Asp Tyr Trp Gly Gln Gly Thr Thr Leu Thr
            100                 105                 110

Val Ser Ser
        115

<210> SEQ ID NO 2
<211> LENGTH: 108
<212> TYPE: PRT
<213> ORGANISM: Mus musculus

<400> SEQUENCE: 2

Leu Thr Gln Ser Pro Ala Ser Leu Ala Val Ser Leu Gly Gln Arg Ala
1               5                   10                  15

Thr Ile Ser Cys Arg Ala Ser Glu Ser Val Asp Asn Tyr Gly Ile Ser
                20                  25                  30

Phe Leu Asn Trp Phe Gln Gln Lys Pro Gly Gln Pro Pro Lys Leu Leu
            35                  40                  45

Ile Tyr Ala Ala Ser Asn Gln Gly Ser Gly Val Pro Ala Arg Phe Ser
        50                  55                  60

Gly Ser Gly Ser Gly Thr Asp Phe Ser Leu Asn Ile His Pro Met Glu
65                  70                  75                  80

Glu Asp Asp Thr Gly Met Tyr Phe Cys Gln Gln Ser Lys Glu Val Pro
                85                  90                  95

Arg Thr Phe Gly Gly Gly Thr Lys Leu Glu Ile Ile
            100                 105
```

<210> SEQ ID NO 3
<211> LENGTH: 10
<212> TYPE: PRT
<213> ORGANISM: Mus musculus

<400> SEQUENCE: 3

Gly Tyr Thr Phe Thr Asn Tyr Trp Met His
1               5                   10

<210> SEQ ID NO 4
<211> LENGTH: 10
<212> TYPE: PRT
<213> ORGANISM: Mus musculus

<400> SEQUENCE: 4

Thr Ile Tyr Pro Gly Asn Ser Asp Thr Asn
1               5                   10

<210> SEQ ID NO 5
<211> LENGTH: 16
<212> TYPE: PRT
<213> ORGANISM: Mus musculus

<400> SEQUENCE: 5

Glu Asp Ser Arg Ser Leu Tyr Tyr Asn Gly Trp Asp Tyr Phe Asp Tyr
1               5                   10                  15

<210> SEQ ID NO 6
<211> LENGTH: 10
<212> TYPE: PRT
<213> ORGANISM: Mus musculus

<400> SEQUENCE: 6

Glu Ser Val Asp Asn Tyr Gly Ile Ser Phe
1               5                   10

<210> SEQ ID NO 7
<211> LENGTH: 4
<212> TYPE: PRT
<213> ORGANISM: Mus musculus

<400> SEQUENCE: 7

Tyr Ala Ala Ser
1

<210> SEQ ID NO 8
<211> LENGTH: 9
<212> TYPE: PRT
<213> ORGANISM: Mus musculus

<400> SEQUENCE: 8

Gln Gln Ser Lys Glu Val Pro Arg Thr
1               5

<210> SEQ ID NO 9
<211> LENGTH: 13
<212> TYPE: PRT
<213> ORGANISM: Artificial sequence
<220> FEATURE:
<223> OTHER INFORMATION: PADRE peptide
<220> FEATURE:
<221> NAME/KEY: misc_feature
<222> LOCATION: (3)..(3)
<223> OTHER INFORMATION: Xaa can be any naturally occurring amino acid

```
<400> SEQUENCE: 9

Ala Lys Xaa Val Ala Ala Trp Thr Leu Lys Ala Ala Cys
1               5                   10

<210> SEQ ID NO 10
<211> LENGTH: 16
<212> TYPE: PRT
<213> ORGANISM: Artificial sequence
<220> FEATURE:
<223> OTHER INFORMATION: Tetanus Toxin peptide

<400> SEQUENCE: 10

Cys Gln Tyr Ile Lys Ala Asn Ser Lys Phe Ile Gly Ile Thr Glu Leu
1               5                   10                  15

<210> SEQ ID NO 11
<211> LENGTH: 8
<212> TYPE: PRT
<213> ORGANISM: Mus musculus

<400> SEQUENCE: 11

Gly Tyr Thr Phe Thr Asn Tyr Trp
1               5

<210> SEQ ID NO 12
<211> LENGTH: 8
<212> TYPE: PRT
<213> ORGANISM: Mus musculus

<400> SEQUENCE: 12

Ile Tyr Pro Gly Asn Ser Asp Thr
1               5
```

TGF-β1 SPECIFIC ANTIBODIES AND METHODS AND USES THEREOF

CROSS REFERENCE TO RELATED APPLICATIONS

The present application is a Divisional of National Stage Application Ser. No. 14/383,602 filed Sep. 8, 2014, now U.S. Pat. No. 9,518,112, claiming the priority of PCT Application No. PCT/US2013/029334 filed Mar. 6, 2013, which in turn, claims priority from U.S. Provisional Application Ser. No. 61/608,393 filed Mar. 8, 2012. Applicants claim the benefits of 35 U.S.C. § 120 as to the PCT Application and priority under 35 U.S.C. § 119 as to the said U.S. Provisional application, and the entire disclosures of both applications are incorporated herein by reference in their entireties.

FIELD OF THE INVENTION

The present invention relates to specific binding members, particularly antibodies and fragments thereof, which bind to transforming growth factor beta 1 (TGF-β1) are provided, particularly recognizing human and mouse TGF-β1 and not recognizing or binding TGF-β2 or TGF-β3. Particular antibodies are provided which specifically recognize and neutralize TGF-β1. These antibodies are useful in the diagnosis and treatment of conditions associated with activated or elevated TGF-β1, including cancer, and for modulating immune cells and immune response, including immune response to cancer or cancer antigens. The antibodies, variable regions or CDR domain sequences thereof, and fragments thereof of the present invention may also be used in therapy in combination with chemotherapeutics, immune modulators, cancer vaccines, cancer antigens, or anti-cancer agents and/or with other antibodies or fragments thereof.

BACKGROUND OF THE INVENTION

Transforming growth factor beta (TGFβ) regulates normal cell processes such as proliferation, differentiation and apoptosis as well as the invasiveness and metastatic spread of cancer cells. The TGF Beta family includes Transforming Growth Factor Beta 1, 2, and 3 (TGF-β1, TGF-β2, and TGF-β3) which are highly pleiotropic cytokines that virtually all cell types secrete. TGF-β molecules act as cellular switches that regulate processes such as immune function, proliferation, and epithelial-mesenchymal transition. TGF-β1 plays an important role in controlling the immune system. TGF-β1 is released by some T cells—regulatory T cells (Tregs)—to inhibit the actions of other T cells. TGF-β1 prevents the activation of quiescent helper T cells and cytotoxic T cells and can inhibit the secretion and activity of cytokines such as IFN-γ, IL-2 and TNF-α (Wahl S et al (1988) J Immunol 140(9):3026-3032; Tiemessen M et al (2003) Int Immunol 15(12):1495-1504; Wahl S et al (2006) Immunol Rev 213:213-227).

TGFβ in Cancer

TGF-β is both a tumor suppressor and a tumor promoter. Indeed, loss or attenuation of TGF-β signaling in epithelial cells and stroma is permissive for epithelial cell transformation (Siegel, P. M. and Massague, J. (2003) Nat Rev Cancer 3:807-820; Bierie, B. and Moses, H. L. (2006) Nat Rev Cancer 6:506-520). On the other hand, introduction of dominant-negative TGF-β receptors into metastatic cancer cells has been shown to inhibit epithelial-to-mesenchymal transdifferentiation, motility, invasiveness, and survival, supporting the tumor promoter role in TGF-β in fully transformed cells (reviewed Dumont, N. and Arteaga, C. L. (2003) Cancer Cell 3:531-536). In addition, excess production and/or activation of TGF-β by cancer cells can contribute to tumor progression by mechanisms involving modulation of the tumor microenvironment (Siegel, P. M. and Massague, J. (2003) Nat Rev Cancer 3:807-820; Wakefield, L. M., and Roberts, A. B. (2002) Curr Opin Genet Dev 12:22-29; Arteaga, C. L. (2006) Curr Opin Genet Dev 16:30-37). These data have provided a rationale in favor of blockade of autocrine/paracrine TGF-β signaling in human cancers with a therapeutic intent. Some tumors resistant to conventional anticancer chemotherapy overexpress TGF-βs (Lui, P et al (2000) Int J Oncol 16:599-610; Teicher, B. A. et al (1997) In Vivo 11:453-461), and inhibitors of TGF-β have been shown to reverse this resistance (Teicher, B. A. et al (1997) In Vivo 11:463-472). In addition, overexpression of TGF-β ligands have been reported in most cancers, and high levels of these in tumor tissues and/or serum are associated with early metastatic recurrences and/or poor patient outcome (Wojtowicz-Praga, S. (2003) Invest New Drugs 21:21-32; Ito, N., et al. (1995) Cancer Lett 89:45-48; Shariat, S. F., et al (2001) Cancer 92:2985-2992; Shariat, S. F., et al (2001) J Clin Oncol 19:2856-2864; Tsushima, H., et al (2001) Clin Cancer Res 7:1258-1262; Rich, J. N. (2003) Front Biosci 8:e245-e260). Animal studies with pan-TGF-β antibody have shown inhibition of tumor recurrence or metastasis in fibrosarcoma, colon cancer, and breast cancer (Terabe M et al (2003) J Exp Med 198:1741-1752; Nam J-S et al (2008) Cancer Res 68(10):3835-3843), and reduced radiation-induced acceleration of metastatic breast cancer (Biswas S et al (2007) 117:1305-1313). It is notable that in radiation studies, thoracic radiation and chemotherapy in metastatic breast cancer models specifically induced plasma TGF-β1 levels (Biswas S et al (2007) 117:1305-1313).

TGF-β and Immunomodulation

Successful treatment of immunotherapy against cancer depends on inducing an integrated and durable immune response to cancer antigens. Evidence indicates that this may be achieved by overcoming the immunosuprressive milieu in the tumor microenvironment attributed to TGFβ-mediated immune suppression. For example, TGFβ suppresses both innate and the adaptive arms of the immune response. Regarding the innate immune response, TGFβ modulates NK cells cytolytic activity. Furthermore, TGFβ also inhibits DC maturation and cytokine production, thereby promoting a tolerogenic environment. In addition, TGFβ produced by tolerogenic DC contributes to Treg cell differentiation. TGFβ can also favor the differentiation of macrophage lineage, an M2 cell, that produces high levels of TGFβ. M2 macrophage competes with DC for antigen but does not present them. Regarding the adaptive immune response, TGFβ mitigates the function of effector CD8 and CD4 T cells by inhibiting T helper and CTL activity and promoting apoptosis of effector T cells. It has been shown that overproduction of TGF-β by tumor cells and Gr1+ CD11b+ myeloid derived suppressor cells leads to evasion of host immune surveillance and tumor progression (Yang L et al (2010) J Bone Miner Res 25(8):1701-1706). Membrane associated TGF-β1 contributes to blockade of activation of memory T-cells that exist in an anergic state within the tumor microenvironment (Broderick L. et al Banket R B (2006) J Immunol 177:3082-3088.) TGF-mediated inhibition of CTL functions during antitumor immunity through several mechanisms. For example, TGFβ directly inhibits CTL function by suppressing the expression of several cytolytic genes, including the genes encoding granzyme A, granzyme B, IFNG and FAS ligand. TGFβ also attenuates the effector function of antigen-specific memory CD8 T cells and blocks TCR signaling of tumor infiltrating lymphocytes and alters cytokine production in CD8 T cells (Ahmadzadeh, M. & Rosenberg, S. A. (2005) J. Immunol. 174:5215-5223; di Bari, M. G. et al. (2009) Cancer Immunol Immunother 58:1809-1818).

In addition to turning off the immune response, TGFβ promotes the differentiation of regulatory T cells (Tregs) and recruites their migration to the tumor site. In human cancers, accumulating data shows that CD4$^+$FOXP3$^+$ Tregs are present in tumor local sites. Sato et al has demonstrated that the ratio of CD8$^+$ T cells to CD4$^+$CD25$^+$FOXP3$^+$ Tregs is an important prognostic indicator, with a low ratio associated with a poor outcome in ovarian cancer patients, indicating the essential role of Treg in protective anti-tumor immune responses (Sato, E et al (2005) PNAS 102(51):18538-18543). Considering the importance of Treg in suppression of anti-tumor immune responses, controlling Tregs is an important and clinically relevant goal. TGFbeta induces development of Treg cells. Since Tregs suppress antitumor immunity, a decreased in the percentage of Tregs in peripheral blood and at the tumor site is evaluated as a biomarker for effective immune therapy.

Blockade of IGFβ signaling leads to the enhancement of NK- and CTL-mediated antitumor activity (Arteaga C L et al (1993) J Clin Invest 92:2569-76; Bollard C M et al (2002) Blood 99:1379-87) In studies in mice, it has been shown that adoptive transfer of tumor-reactive, TGF-β-insensitive CD8+ T cells, rendered insensitive by retroviral mediated gene therapy with a dominant negative TGF-β receptor, into immunocompetent mice was able to eradicate lung metastasis of mouse prostate cancer (Zhang Q, et al (2005) Cancer Res 65:1761-9; Zhang, Q et al (2006) Mol Cancer Ther 5:1733-1743). Generic blockade of TGF-β response in mice inhibited prostate cancer metastasis, but led to widespread inflammatory disease in the animals (Shah A H, et al (2002) J Immunol 169:3485-91).

Targeting TGFβ with Neutralizing Antibodies to Enhance Cancer Immunotherapy

Evidence of TGFβ production by tumor cells and by myeloid-derived suppressor cells (MDSC) present at the tumor site along with TGFβ immune suppressive activity at the tumor site strongly supports that blocking TGFβ can enhance antigen uptake, presentation, and activation of antitumor immune response mediated by therapeutic vaccines. Indeed, recent studies have demonstrated that blockade of TGF-β, using mouse TGF-β generic antibody 1D11 (which recognizes TGF-β1, TGF-β2 and TGF-β3), synergistically enhances tumor vaccines in animal models via CD8$^+$ T cells (Terabe M et al (2009) Clin Cancer Res 15:6560-6569; Takaku S et al (2010) Int J Cancer 126(7): 1666). Evaluating immunological indicators such as an activation of effector T-cells within the tumor compartment in patients receiving these therapies can serve as biomarkers or biosignature for monitoring immune-mediated killing of tumor cells and response to therapy.

TGFβ isoforms (β1, β2, and β3) are involved in many biological processes, therefore, antibodies that bind all three isoforms of TGFβ may potentiate autoimmune toxicity. To minimize toxicity, antibody that binds specifically to TGFβ1 may be better tolerated. Treatment of cancer or other TGFβ-mediated disorders may be improved by use of a neutralization antibody that only binds to TGFβ-1.

Accordingly, it would be desirable to develop TGFβ-1 specific antibodies, particularly antibodies which can be utilized in mouse animal models and which demonstrate increased efficacy and applicability in diagnosis and therapy, and it is toward the achievement of that objective that the present invention is directed.

The citation of references herein shall not be construed as an admission that such is prior art to the present invention.

SUMMARY OF THE INVENTION

In a general aspect, the present invention provides novel TGF-β antibodies directed specifically against human TGF-β1 and which do not cross react/bind to other members of the TGF-beta family, and particularly do not cross react or bind to TGF-β2 or to TGF-β3. In a broad aspect, the present invention provides an isolated specific binding member, particularly an antibody or fragment thereof, including an Fab fragment and a single chain or domain antibody, which specifically recognizes TGF-β1. In a particular aspect, the antibody or active fragment thereof, neutralizes TGF-β1 activity.

The invention provides antibodies specifically directed against transforming growth factor (TGF) beta 1 (TGFβ1) for diagnostic and therapeutic purposes. In particular, antibodies specific for TGFβ1 are provided, wherein said antibodies recognize and are capable of binding human and mouse TGFβ1, and do not recognize other forms of TGF-beta, TGF-β2 or TGF-β3. The antibodies of the present invention have diagnostic and therapeutic use in cancer and in immune modulation, including modulating the immune response to cancer and in cancer vaccines. The antibodies of the invention are applicable in characterizing and in modulating the activity of TGF-β1, particularly in neutralizing TGF-β1 activity.

In a particular aspect the antibodies of the invention are applicable in treatment, management and/or prevention of cancers, including in cancer recurrence and metastasis. The antibodies are applicable for use relative to cancer, including adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor. The antibodies have applicability in therapeutic treatment or management of cancer. The antibodies have applicability in enhancing the anti-cancer immune response and in enhancing cancer vaccines.

In a further aspect, the present invention provides an antibody or fragment thereof, which recognizes TGF-β1 and is selected from antibodies 4C3.7, 8D6, 19D8, 4A11, 19H11, 21C11, 13A1 and 4G9. In a particular aspect the invention provides an antibody or active fragment thereof that recognizes and neutralizes TGF-β1 and is selected from antibodies 4C3.7, 19D8, 13A1 and 4G9.

In a particular aspect, the invention provides anti-TGF-β1 specific antibody 13A1. In a further particular aspect the invention provides TGF-β1 specific antibody capable of specifically binding and neutralizing TGF-β1 comprising the heavy chain amino acid sequence (SEQ ID NO: 1) as set out in FIG. 1. In one such aspect, the invention provides a TGF-β1 antibody comprising the heavy chain variable region CDR sequences set out in FIG. 1. In an aspect thereof TGF-β1 specific antibody is provided having a heavy chain variable region comprising the CDR 1, CDR2 and CDR3 domain amino acid sequences of GYTFTNYWMH (SEQ ID NO: 3), TIYPGNSDTN (SEQ ID NO: 4) and EDSRSLYYNGWDYFDY (SEQ ID NO: 5) respectively. In an aspect, the TGF-β1 specific antibody is provided having a heavy chain variable region comprising the CDR 1, CDR2 and CDR3 domain amino acid sequences of GYTFTNYW (SEQ ID NO: 11), IYPGNSDT (SEQ ID NO: 12) and EDSRSLYYNGWDYFDY (SEQ ID NO: 5) respectively, wherein a shorter accepted CDR1 and CDR2 domain amino acid sequence is specified.

The antibody of the invention may comprise the heavy chain variable region amino acid sequence set out in FIG. 1 or the heavy chain CDR domain region CDR1, CDR2 and CDR3 sequences of FIG. 1, and a light chain variable region. In an aspect the light chain variable region sequence is a sequence comprising amino acid sequence from the light chain sequence of FIG. 1. In an aspect the TGF-β1 antibody comprises the light chain amino acid sequence (SEQ ID NO: 2) as set out in FIG. 1. In one such aspect, the invention provides a TGF-β1 antibody comprising the light chain variable region CDR sequences set out in FIG. 1. In an aspect thereof TGF-β1 specific antibody is provided having a light chain variable region comprising the CDR 1, CDR2 and CDR3 domain amino acid sequences of ESVDNYGISF (SEQ ID NO: 6), YAAS (SEQ ID NO: 7) and QQSKEVPRT (SEQ ID NO: 8) respectively.

In a particular aspect, TGF-β1 specific antibody is provided wherein said antibody comprises the heavy chain CDR sequences of FIG. 1 (SEQ ID NOS: 3, 4 and 5) and the light chain CDR sequences of FIG. 1 (SEQ ID NOS: 6, 7 and 8). In one such aspect, a TGF-β1 antibody of the invention comprises the heavy chain variable region amino acid sequence as set out in FIG. 1 (SEQ ID NO: 1) and the light chain variable region amino acid sequence as set out in FIG. 1 (SEQ ID NO: 2). In an aspect, the TGF-β1 specific antibody of the invention comprises a heavy chain variable region comprising the CDR 1, CDR2 and CDR3 domain amino acid sequences of GYTFTNYW (SEQ ID NO: 11), IYPGNSDT (SEQ ID NO: 12) and EDSRSLYYNGWDYFDY (SEQ ID NO: 5) respectively, wherein a shorter accepted CDR1 and CDR2 domain amino acid sequence is specified. A TGF-β1 antibody of the invention, capable of specifically binding TGF-β1 and which does not bind TGF-β2 or TGF-β3, may comprise an amino acid sequence having at least 90% amino acid identity to the heavy chain variable region amino acid sequence (SEQ ID NO: 1) and the light chain variable region amino acid sequence (SEQ ID NO: 2) as set out in FIG. 1.

In an aspect of the invention, the antibody or fragment of the invention neutralizes TGF-β1, and particularly specifically neutralizes TGF-β1 and does not neutralize TGF-β2 or TGF-β3. In a particular aspect, the antibody or active fragment thereof of the present invention neutralizes human and mouse TGF-β1. In an aspect, antibody of the invention neutralizes and blocks TGF-β1-mediated signaling in vivo in a mammal, particularly in a human or in a mouse.

The binding of an antibody to its target antigen is mediated through the complementarity-determining regions (CDRs) of its heavy and light chains. Accordingly, specific binding members based on the CDR regions of the heavy or light chain, and preferably both, of the antibodies of the invention, particularly of antibody 13A1, will be useful specific binding members for therapy and/or diagnostics. The heavy chain variable region amino acid sequence and CDRs of the antibody 13A1 are depicted in FIG. 1. Antibody 13A1 comprises heavy chain CDR sequences CDR1 GYTFTNYWMH (SEQ ID NO: 3), CDR2 TIYPGNSDTN (SEQ ID NO: 4) and CDR3 EDSRSLYYNGWDYFDY (SEQ ID NO: 5). Light chain variable region amino acid sequence of antibody 13A, including sequence of the light chain CDR sequences is provided in FIG. 1. In an aspect, the binding member or antibody, including antibody 13A1, is provided having a heavy chain variable region comprising the CDR 1, CDR2 and CDR3 domain amino acid sequences of GYTFTNYW (SEQ ID NO: 11), IYPGNSDT (SEQ ID NO: 12) and EDSRSLYYNGWDYFDY (SEQ ID NO: 5) respectively, wherein a shorter accepted CDR1 and CDR2 domain amino acid sequence is specified. Antibody 13A1 comprises light chain CDR sequences CDR1 ESVDNYGISF (SEQ ID NO: 6), CDR2 YAAS (SEQ ID NO: 7) and CDR3 QQSKEVPRT (SEQ ID NO: 8).

Accordingly, specific binding proteins such as antibodies which are based on the CDRs of the antibody(ies), particularly including the heavy chain CDRs identified herein, will be useful for targeting TGF-β1, particularly TGF-β1 expressing cells, or TGF-β1 activity in immune response, in diseases or in cancers. As the target of the antibodies of the invention is specifically TGF-β1 and not TGF-β2 and/or TGF-β3 the antibodies of the invention do no significantly bind to TGF-β forms or family members other TGF-β and it is anticipated that there will be less toxicity and inflammatory response or untoward immune response or reaction in cell targets or in animals with the present TGF-β1 specific antibodies, particularly as compared to a pan-TGF-β antibody which recognizes more than one or all forms of TGF-β.

In further aspects, the invention provides an isolated nucleic acid which comprises a sequence encoding a specific binding member or antibody as defined above, and methods of preparing specific binding members or antibodies of the invention which comprise expressing said nucleic acids under conditions to bring about expression of said binding member or antibody, and recovering the binding member or antibody. In one such aspect, a nucleic acid encoding antibody variable region sequence having the heavy chain amino acid sequences as set out in FIG. 1 is provided or an antibody having heavy chain CDR domain sequences as set out in FIG. 1 is provided. In an aspect, nucleic acid encoding an antibody light chain variable region having amino acid sequence comprising sequence of light chain sequence of FIG. 1 is provided. The present invention also relates to a recombinant DNA molecule or cloned gene, or a degenerate variant thereof, which encodes an antibody of the present invention; preferably a nucleic acid molecule, in particular a recombinant DNA molecule or cloned gene, encoding the antibody VH, particularly the CDR region sequences, which is capable of encoding a sequence shown in FIG. 1.

The unique specificity and affinity of the antibodies and fragments of the invention provides diagnostic and therapeutic uses to identify, characterize and target conditions associated with TGF-β1 expression, activity or activation. In particular, antibodies of the invention targeting TGF-β1 are useful in modulating immune response. In an aspect thereof, antibodies of the invention targeting TGF-β1 are useful in modulating immune response against cancer, cancer or tumor cells, and cancer or tumor antigens. Applicable conditions include infectious disease, cancers, host immune response including in transplant and transplantation, and immune diseases or disorders, such as autoimmune diseases or inflammatory conditions. Applicable cancers include adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

Evidence of TGFβ production by tumor cells and by myeloid-derived suppressor cells along with TGFβ immune suppressive activity at the tumor site strongly supports that blocking TGFβ, particularly specifically blocking TGF-β1, can enhance antigen uptake, presentation, and activation of antitumor immune response mediated by therapeutic vaccines. Thus, in an aspect of the invention TGF-β1 antibody(ies), particularly TGF-β1 neutralizing antibody(ies), may be administered in conjunction with or in a composition of cancer antigen(s) and adjuvant(s), including to patients to promote a more robust priming and activation of the adaptive anti-tumor response to enhance immune therapies directed at cancers. Additional inhibitors to TGFβ activity, such as small molecules, antisense or aptamers can also be used to inhibit TGFβ activity.

Evidence of potent anti-tumor immunity requires modulating multiple arms of host immune response and targeting pathways that contributes to tumor cell growth and survival. Combination agents that modulate immune response and arrest tumor growth and progression can generate anticancer immunity and arrest tumor growth to improve clinical outcomes (Vanneman, M (2012) Nature Reviews Cancer (12):237-251). Thus, in an aspect of the invention anti-TGF-β1 antibody(ies) may be administered alone or in combination with other treatments, therapeutics or agents either simultaneously or sequentially dependent upon the condition to be treated Immune modulators may be included in a composition with or administered with TGF-β1 antibody(ies) and/or at different time from which TGF-β1 antibody(ies) are administered to enhance immune modulation and/or cancer therapy, including immune therapies directed against cancer. Applicable immune modulators include IDO, TDO (Platten M (2012) Cancer Research 72(21):5435-40), α-galactosyl ceramide and analogs thereof such as IMM47, TLR ligands such as poly I:C (TLR3), MPL (TLR4), imiquimod (TLR7), R848 (TLR8) or CpG (TLR9), iCOS, CTLA-4, PD1, PD1 ligand, OX40 and OX40 ligand, Lag3, GITR, GITR ligand interleukins, tumor necrosis factor (TNF) or other growth factors, colony stimulating factors, T cell modulators including modulators of $CD8^+$ T cells, cytokines or hormones such as dexamethasone which stimulate the immune response or reduction or elimination of cancer cells or tumors (Mellman I (2011) Nature (480): 480-489). Additional immunmodulators are small molecules, antagonist antibodies or agonist antibodies targeting the applicable immune modulators including IDO, TDO, Toll like receptor family or iCOS, CTLA-4, PD1, PD1 ligand, OX40 and OX40 ligand, interleukins, tumor necrosis factor (TNF) or other growth factors, colony stimulating factors, T cell modulators including modulators of $CD8^+$ T cells, cytokines which stimulate the immune response or reduction or elimination of cancer cells or tumors.

Additional immune modulators, including TLR ligands such as poly I:C (TLR3), MPL (TLR4), imiquimod (TLR7), R848 (TLR8) or CpG (TLR9) can be used in combination with TGF-β1 specific neutralizing antibody to produce an enhanced immune stimulation and resulting protection from conditions in which it is desirable for the immune system to respond effectively such as infectious disease or cancer.

TGF-β1 specific antibody(ies) can also be used as immunostimulant(s) or adjuvant(s) in combined use with antigen materials such as, without limitation, proteins, peptides, or nucleic acids and so forth in order to produce a protective immune response, such as a B-cell and IgG antibody response to the administered antigen. TGF-β1 specific antibody(ies) can also be used as immunostimulant(s) or adjuvant(s) in combined use with antigen materials such as, without limitation, proteins, peptides, or nucleic acids and so forth in order to produce a protective immune response, such as a T-cell or CTL response to the administered antigen.

Such antigen materials could be and may include any materials suitable for prevention or therapy of a/the particular disease. Specifically, with regards to cancer, examples of tumor associated peptide and protein antigens that can be administered to induce or enhance an immune response are derived from tumor associated genes and encoded proteins including MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-A13, GAGE-1, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (MAGE-B4), tyrosinase, brain glycogen phosphorylase, Melan-A, MAGE-C1, MAGE-C2, NY-ESO-1, LAGE-1, SSX-1, SSX-2(HOM-MEL-40), SSX-1, SSX-4, SSX-5, SCP-1 and CT-7. For example, antigenic peptides characteristic of tumors include those listed in published PCT application WO00/20581 (PCT/US99/21230).

TGF-β1 specific antibodies are efficacious both in vitro and in vivo as has been shown. Hence, one aspect of the invention relates to stimulating an immune response in a subject, by administering TGF-β1 specific antibody with or without an antigenic molecule, in an amount sufficient to stimulate a favorable immunologic response in such subject.

The invention includes compositions and or kits, comprising one or more TGF-β1 specific antibody together with one or more immunogenic proteins or peptides. The compositions include pharmaceutical compositions and immunological compositions.

The antibodies, fragments thereof and recombinant antibodies comprising the CDR domains according to the invention may be used in a method of treatment or diagnosis of the human or animal body, such as a method of treatment of a tumor in a human patient which comprises administering to said patient an effective amount of the antibodies, fragments thereof and recombinant antibodies of the invention. The antibodies, fragments thereof and recombinant antibodies comprising the CDR domains according to the invention may be used in a method of stimulating or enhancing an immune response to cancer, tumor cells or cancer or tumor antigen(s) in a mammal, particularly in a human, comprises administering to said mammal an effective amount of the antibodies, fragments thereof and recombinant antibodies of the invention. The antibodies, fragments thereof and recombinant antibodies comprising the CDR domains according to the invention may be used in a method of inhibiting or reducing recurrence or metastasis of cancer in a mammal, particularly in a human, comprises administering to said mammal an effective amount of the antibodies, fragments thereof and recombinant antibodies of the invention. The antibodies, fragments thereof and recombinant antibodies comprising the CDR domains according to the invention may be used in a method of inhibiting or blocking stimulation of TGFβ, particularly TGFβ1, in response to radiation or cancer therapy in a mammal, particularly in a human, comprises administering to said mammal an effective amount of the antibodies, fragments thereof and recombinant antibodies of the invention.

A therapeutic method is associated with the prevention or treatment of cancer, or the stimulation or enhancement of immune response to cancer, including but not limited to adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

The binding members and antibodies of the present invention, and in a particular embodiment the antibody having sequence represented in FIG. 1, or active fragments thereof, and single chain, recombinant or synthetic antibodies derived therefrom, particularly comprising the heavy chain CDR region sequences and the light chain CDR region sequences depicted in FIG. 1, can be prepared in pharmaceutical compositions, including a suitable vehicle, carrier or diluent, or including an adjuvant and/or immune modulator, for administration in instances wherein therapy is appropriate, such as to treat cancer or stimulant or enhance immune response, including immune response against cancer. Such pharmaceutical compositions may also include means for modulating the half-life of the binding members, antibodies or fragments by methods known in the art such as pegylation. Such pharmaceutical compositions may further comprise additional antibodies or therapeutic agents.

A composition of the present invention may be administered alone or in combination with other treatments, therapeutics or agents, either simultaneously or sequentially dependent upon the condition to be treated. In addition, the present invention contemplates and includes compositions comprising the binding member, particularly antibody or fragment thereof, herein described and other agents or therapeutics such as anti-cancer agents or therapeutics, anti-mitotic agents, apoptotic agents or antibodies, or immune modulators, or small molecule inhibitiors to immune modulators. More generally these anti-cancer agents may be tyrosine kinase inhibitors or phosphorylation cascade inhibitors, post-translational modulators, cell growth or division inhibitors (e.g. anti-mitotics), inhibitors or signal transduction inhibitors. Other treatments or therapeutics may include the administration of suitable doses of pain relief drugs such as non-steroidal anti-inflammatory drugs (e.g. aspirin, paracetamol, ibuprofen or ketoprofen) or opiates such as morphine, or anti-emetics. In addition, the composition may be administered with immune modulators, such as α-galactosyl ceramide, interleukins, tumor necrosis factor (TNF) or other growth factors, colony stimulating factors, cytokines or hormones such as dexamethasone which stimulate the immune response and reduction or elimination of cancer cells or tumors. The composition may also be administered with, or may include combinations along with other anti-TGFβ antibodies, other immunomodulatory antibodies or other anti-tumor antigen antibodies.

The present invention also includes antibodies and fragments thereof, which are covalently attached to or otherwise associated with other molecules or agents. These other molecules or agents include, but are not limited to, molecules (including antibodies or antibody fragments) with distinct recognition characteristics, toxins, ligands, and chemotherapeutic agents. In an additional aspect the antibodies or fragments of the invention may be used to target or direct therapeutic molecules or other agents, for example to target molecules or agents to TGFβ expressing cells, or TGFβ responsive cells, for example cells at wound sites, tumor sites, inflammatory areas or cancerous lesions.

The diagnostic utility of the present invention extends to the use of the antibodies of the present invention in assays to characterize tumors or cellular samples or to screen for tumors or cancer, including in vitro and in vivo diagnostic assays. In an immunoassay, a control quantity of the antibodies, or the like may be prepared and labeled with an enzyme, a specific binding partner and/or a radioactive element, and may then be introduced into a cellular sample. After the labeled material or its binding partner(s) has had an opportunity to react with sites within the sample, the resulting mass may be examined by known techniques, which may vary with the nature of the label attached.

Specific binding members of the invention may carry a detectable or functional label. The specific binding members may carry a radioactive label, such as the isotopes $^{3}H$, $^{14}C$, $^{32}P$, $^{35}S$, $^{36}Cl$, $^{51}Cr$, $^{57}Co$, $^{58}Co$, $^{58}Fe$, $^{90}Y$, $^{121}I$, $^{124}I$, $^{125}I$, $^{131}I$, $^{111}In$, $^{117}Lu$, $^{221}At$, $^{198}Au$, $^{67}Cu$, $^{225}Ac$, $^{213}Bi$, $^{99}Tc$ and $^{186}Re$. When radioactive labels are used, known currently available counting procedures may be utilized to identify and quantitate the specific binding members. In the instance where the label is an enzyme, detection may be accomplished by any of the presently utilized colorimetric, spectrophotometric, fluorospectrophotometric, amperometric or gasometric techniques known in the art.

The radiolabelled specific binding members, particularly antibodies and fragments thereof, are useful in in vitro diagnostics techniques and in in vivo radioimaging techniques. In a further aspect of the invention, radiolabelled specific binding members, particularly antibodies and fragments thereof, particularly radioimmunoconjugates, are useful in radioimmunotherapy, particularly as radiolabelled antibodies for cancer therapy. In a still further aspect, the radiolabelled specific binding members, particularly antibodies and fragments thereof, are useful in radioimmunoguided surgery techniques, wherein they can identify and indicate the presence and/or location of cancer cells, precancerous cells, tumor cells, and hyperproliferative cells, prior to, during or following surgery to remove such cells.

Immunoconjugates or antibody fusion proteins of the present invention, wherein the specific binding members, particularly antibodies and fragments thereof, of the present invention are conjugated or attached to other molecules or agents further include, but are not limited to binding members conjugated to a chemical ablation agent, toxin, immunomodulator, cytokine, cytotoxic agent, chemotherapeutic agent or drug.

The present invention includes an assay system which may be prepared in the form of a test kit for the quantitative analysis of the extent of the presence of, for instance, TGFβ1. The system or test kit may comprise a labeled component prepared by one of the radioactive and/or enzymatic techniques discussed herein, coupling a label to the antibody, and one or more additional immunochemical reagents, at least one of which is a free or immobilized components to be determined or their binding partner(s).

Other objects and advantages will become apparent to those skilled in the art from a review of the ensuing detailed description, which proceeds with reference to the following illustrative drawings, and the attendant claims.

BRIEF DESCRIPTION OF THE DRAWINGS

FIGS. 1A and 1B: (A) provides the TGF-beta1 antibody 13A1 variable region amino acid heavy chain sequence (SEQ ID NO: 1) and light chain sequence (SEQ ID NO: 2); (B) provides the heavy chain CDRs domain sequences CDR1, CDR2 and CDR3 (SEQ ID NOS: 3-5) and the light chain CDRs domain sequences CDR1, CDR2 and CDR3 (SEQ ID NOS: 6-8) for antibody 13A1.

DETAILED DESCRIPTION

Figure 2:
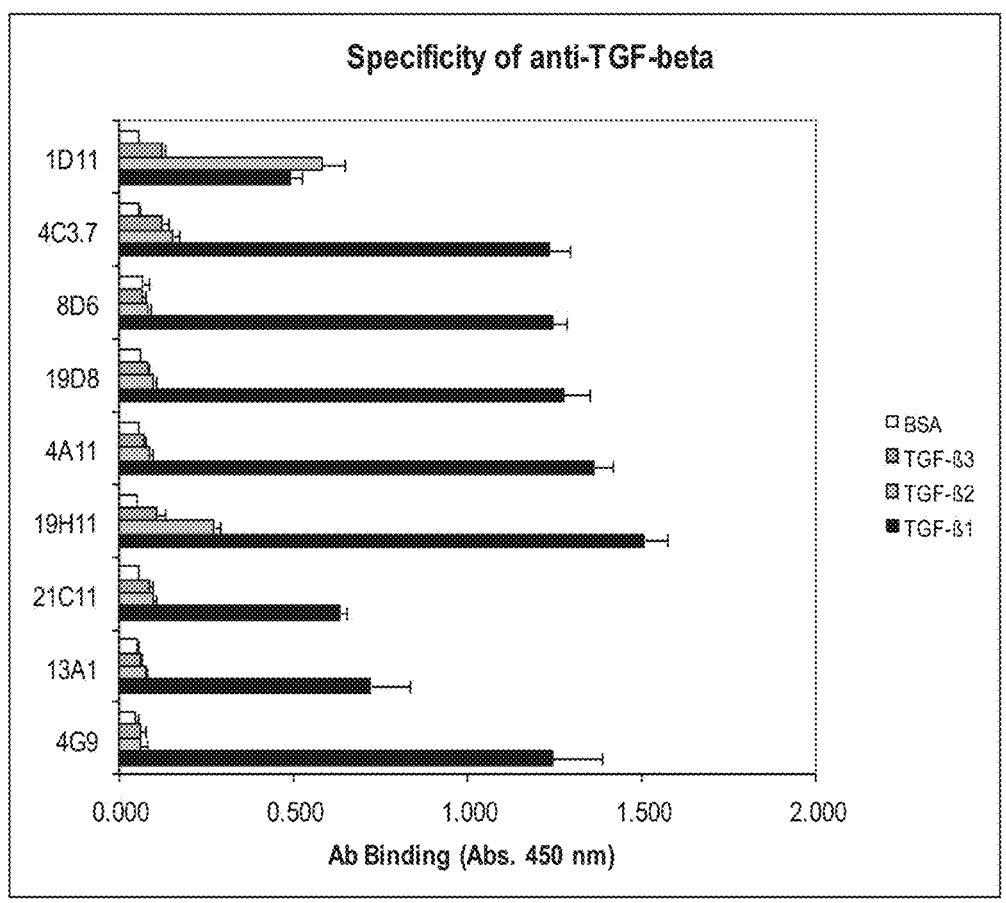
FIG. 2 depicts binding of the TGF-beta1 antibodies to human TGF-beta isotypes β1, β2 and β3.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A. TERMINOLOGY

The term "specific binding member" describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organisation of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. This application is concerned with antigen-antibody type reactions.

The term "antibody" describes an immunoglobulin whether natural or partly or wholly synthetically produced. The term also covers any polypeptide or protein having a binding domain which is, or is homologous to, an antibody binding domain. CDR grafted antibodies are also contemplated by this term. An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567. The term "antibody(ies)" includes a wild type immunoglobulin (Ig) molecule, generally comprising four full length polypeptide chains, two heavy (H) chains and two light (L) chains, or an equivalent Ig homologue thereof (e.g., a camelid nanobody, which comprises only a heavy chain); including full length functional mutants, variants, or derivatives thereof, which retain the essential epitope binding features of an Ig molecule, and including dual specific, bispecific, multispecific, and dual variable domain antibodies; Immunoglobulin molecules can be of any class (e.g., IgG, IgE, IgM, IgD, IgA, and IgY), or subclass (e.g., IgG1, IgG2, IgG3, IgG4, IgA1, and IgA2). Also included within the meaning of the term "antibody" are any "antibody fragment".

An "antibody fragment" means a molecule comprising at least one polypeptide chain that is not full length, including (i) a Fab fragment, which is a monovalent fragment consisting of the variable light (VL), variable heavy (VH), constant light (CL) and constant heavy 1 (CH1) domains; (ii) a F(ab')2 fragment, which is a bivalent fragment comprising two Fab fragments linked by a disulfide bridge at the hinge region; (iii) a heavy chain portion of an Fab (Fd) fragment, which consists of the VH and CH1 domains; (iv) a variable fragment (Fv) fragment, which consists of the VL and VH domains of a single arm of an antibody, (v) a domain antibody (dAb) fragment, which comprises a single variable domain (Ward, E. S. et al., Nature 341, 544-546 (1989)); (vi) a camelid antibody; (vii) an isolated complementarity determining region (CDR); (viii) a Single Chain Fv Fragment wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (ix) a diabody, which is a bivalent, bispecific antibody in which VH and VL domains are expressed on a single polypeptide chain, but using a linker that is too short to allow for pairing between the two domains on the same chain, thereby forcing the domains to pair with the complementarity domains of another chain and creating two antigen binding sites (WO94/13804; P. Holliger et al Proc. Natl. Acad. Sci. USA 90 6444-6448, (1993)); and (x) a linear antibody, which comprises a pair of tandem Fv segments (VH-CH1-VH-CH1) which, together with complementarity light chain polypeptides, form a pair of antigen binding regions; (xi) multivalent antibody fragments (scFv dimers, trimers and/or tetramers (Power and Hudson, J Immunol. Methods 242: 193-204 9 (2000)); (xii) a minibody, which is a bivalent molecule comprised of scFv fused to constant immunoglobulin domains, CH3 or CH4, wherein the constant CH3 or CH4 domains serve as dimerization domains (Olafsen T et al (2004) Prot Eng Des Sel 17(4):315-323; Hollinger P and Hudson P J (2005) Nature Biotech 23(9): 1126-1136); and (xiii) other non-full length portions of heavy and/or light chains, or mutants, variants, or derivatives thereof, alone or in any combination.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023 and U.S. Pat. Nos. 4,816,397 and 4,816,567.

An "antibody combining site" is that structural portion of an antibody molecule comprised of light chain or heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Antibodies may also be bispecific, wherein one binding domain of the antibody is a specific binding member of the invention, and the other binding domain has a different specificity, e.g. to recruit an effector function or the like. Bispecific antibodies of the present invention include wherein one binding domain of the antibody is a specific binding member of the present invention, including a fragment thereof, and the other binding domain is a distinct antibody or fragment thereof, including that of a distinct anti-cancer or anti-tumor specific antibody. The other binding domain may be an antibody that recognizes or targets a particular cell type, as in a neural or glial cell-specific antibody. In the bispecific antibodies of the present invention the one binding domain of the antibody of the invention may be combined with other binding domains or molecules which recognize particular cell receptors and/or modulate cells in a particular fashion, as for instance an immune modulator (e.g., interleukin(s)), a growth modulator or cytokine or a toxin (e.g., ricin) or anti-mitotic or apoptotic agent or factor. Thus, the TGFbeta-1 antibodies of the invention may be utilized to direct or target agents, labels, other molecules or compounds or antibodies in indications such as wound healing, inflammation, cancer or tumors.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may also contain an antibody molecule having a plurality of antibody combining sites, each immunospecific for a different antigen; e.g., a bispecific (chimeric) monoclonal antibody.

The term "antigen binding domain" describes the part of an antibody which comprises the area which specifically binds to and is complementary to part or all of an antigen. Where an antigen is large, an antibody may bind to a particular part of the antigen only, which part is termed an epitope. An antigen binding domain may be provided by one or more antibody variable domains. Preferably, an antigen binding domain comprises an antibody light chain variable region (VL) and an antibody heavy chain variable region (VH).

Immunoconjugates or antibody fusion proteins of the present invention, wherein the antibodies, antibody molecules, or fragments thereof, of use in the present invention are conjugated or attached to other molecules or agents further include, but are not limited to such antibodies, molecules, or fragments conjugated to a chemical ablation agent, toxin, immunomodulator, cytokine, cytotoxic agent, chemotherapeutic agent, antimicrobial agent or peptide, cell wall and/or cell membrane disrupter, or drug.

The term "adjuvant(s)" describes a substance, compound, agent or material useful for improving an immune response or immune cell or component stimulation, and may in some instances be combined with any particular antigen in an immunological, pharmaceutical or vaccine composition. Adjuvants can be used to increase the amount of antibody and effector T cells produced and to reduce the quantity of antigen or immune stimulant or modulator and the frequency of injection. Although some antigens are administered without an adjuvant, there are many antigens that lack sufficient immunogenicity to stimulate a useful immune response in the absence of an effective adjuvant. Adjuvants also improve the immune response from "self-sufficient" antigens, in that the immune response obtained may be increased or the amount of antigen administered may be reduced. An adjuvant can serve as a tissue depot that slowly releases the antigen and also as a lymphoid system activator that nonspecifically enhances the immune response (Hood et al., *Immunology, Second Ed.,* 1984, Benjamin/Cummings: Menlo Park, Calif., p. 384). In a preferred aspect an adjuvant is physiologically and/or pharmaceutically acceptable in a mammal, particularly a human. The standard adjuvant for use in laboratory animals is Freund's adjuvant. Freund's Complete adjuvant (FCA) is an emulsion containing mineral oil and killed mycobacteria in saline. Freund's incomplete adjuvant (FIA) omits the mycobacteria. Both FIA and FCA induce good humoral (antibody) immunity, and FCA additionally induces high levels of cell-mediated immunity. However, neither FCA nor FIA are acceptable for clinical use due to the side effects. In particular, mineral oil is known to cause granulomas and abscesses, and *Mycobacterium tuberculosis* is the agent responsible for tuberculosis. Previously known and utilized adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvant such as BCG (bacille Calmette-Guerin) and *Corynebacterium parvum*. Mineral salt adjuvants include but are not limited to: aluminum hydroxide, aluminum phosphate, calcium phosphate, zinc hydroxide and calcium hydroxide. Preferably, the adjuvant composition further comprises a lipid of fat emulsion comprising about 10% (by weight) vegetable oil and about 1-2% (by weight) phospholipids. Preferably, the adjuvant composition further optionally comprises an emulsion form having oily particles dispersed in a continuous aqueous phase, having an emulsion forming polyol in an amount of from about 0.2% (by weight) to about 49% (by weight), optionally a metabolizable oil in an emulsion-forming amount of up to 15% (by weight), and optionally a glycol ether-based surfactant in an emulsion-stabilizing amount of up to about 5% (by weight). There have been many substances that have been tried to be used as adjuvants, such as the lipid-A portion of gram negative bacterial endotoxin, and trehalose dimycolate of mycobacteria. The phospholipid lysolecithin exhibited adjuvant activity (Arnold et al., Eur. J Immunol. 9:363-366, 1979). Some synthetic surfactants exhibited adjuvant activity, including dimethyldioctadecyl ammonium bromide (DDA) and certain linear polyoxypropylenepolyoxyethylene (POP-POE) block polymers (Snippe et al., Int. Arch. Allergy Appl. Immunol. 65:390-398, 1981; and Hunter et al., J. Immunol. 127:1244-1250, 1981).

The term "specific" may be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

The term "comprise" generally used in the sense of include, that is to say permitting the presence of one or more features or components.

The term "consisting essentially of" refers to a product, particularly a peptide sequence, of a defined number of residues which is not covalently attached to a larger product. In the case of the peptide of the invention referred to above, those of skill in the art will appreciate that minor modifications to the N- or C-terminal of the peptide may however be contemplated, such as the chemical modification of the terminal to add a protecting group or the like, e.g. the amidation of the C-terminus.

The term "isolated" refers to the state in which specific binding members of the invention, or nucleic acid encoding such binding members will be, in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy.

As used herein, "pg" means picogram, "ng" means nanogram, "ug" or "μg" mean microgram, "mg" means milligram, "ul" or "μl" mean microliter, "ml" means milliliter, "l" means liter.

The terms "antibody", "anti-TGFβ1 antibody", "TGF-beta1 antibody", "TGF-β1 antibody", "human/mouse TGFβ1 antibody", and any variants not specifically listed, may be used herein interchangeably, and as used throughout the present application and claims refer to proteinaceous material including single or multiple proteins, and extends to those proteins having the amino acid sequence data described herein and presented in FIG. 1 and the profile of activities set forth herein and in the Claims. Exemplary such TGFβ1 antibodies provided herein include antibodies 4C3.7, 8D6, 19D8, 4A11, 19H11, 21C11, 13A1 and 4G9 as provided and characterized herein. Exemplary antibody 13A1 is particularly characterized herein and extends to antibodies or proteins, including antibody fragments, having the amino acid sequence data described herein and presented in FIG. 1 and the profile of activities set forth herein and in the Claims. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "antibody", "anti-TGFβ1 antibody", "TGFbeta1 antibody", "TGF-β1 antibody", "human/mouse TGFβ1 antibody", and the exemplary antibodies 4C3.7, 8D6, 19D8, 4A11, 19H11, 21C11, 13A1 and 4G9, particularly including antibody 13A1, are intended to include within their scope proteins specifically recited herein as well as all substantially homologous analogs and allelic variations.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |

-continued

TABLE OF CORRESPONDENCE

| SYMBOL | | AMINO ACID |
|---|---|---|
| 1-Letter | 3-Letter | |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease Si), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding specific binding members (antibodies) of the invention which code for e.g. an antibody having amino acid sequence as provided in FIG. 1, or comprising the CDR domain region sequences set out herein or in FIG. 1 but which are degenerate thereto. By "degenerate to" is meant that a different three-letter codon is used to specify a particular amino acid. It is well known in the art that the following codons can be used interchangeably to code for each specific amino acid:

| | |
|---|---|
| Phenylalanine (Phe or F) | UUU or UUC |
| Leucine (Leu or L) | UUA or UUG or CUU or CUC or CUA or CUG |
| Isoleucine (Ile or I) | AUU or AUC or AUA |
| Methionine (Met or M) | AUG |
| Valine (Val or V) | GUU or GUC of GUA or GUG |
| Serine (Ser or S) | UCU or UCC or UCA or UCG or AGU or AGC |
| Proline (Pro or P) | CCU or CCC or CCA or CCG |
| Threonine (Thr or T) | ACU or ACC or ACA or ACG |
| Alanine (Ala or A) | GCU or GCG or GCA or GCG |
| Tyrosine (Tyr or Y) | UAU or UAC |
| Histidine (His or H) | CAU or CAC |
| Glutamine (Gln or Q) | CAA or CAG |
| Asparagine (Asn or N) | AAU or AAC |
| Lysine (Lys or K) | AAA or AAG |
| Aspartic Acid (Asp or D) | GAU or GAC |
| Glutamic Acid (Glu or E) | GAA or GAG |
| Cysteine (Cys or C) | UGU or UGC |
| Arginine (Arg or R) | CGU or CGC or CGA or CGG or AGA or AGG |

-continued

| | |
|---|---|
| Glycine (Gly or G) | GGU or GGC or GGA or GGG |
| Tryptophan (Trp or W) | UGG |
| Termination codon | UAA (ochre) or UAG (amber) or UGA (opal) |

It should be understood that the codons specified above are for RNA sequences. The corresponding codons for DNA have a T substituted for U.

Mutations can be made in the sequences encoding the amino acids, antibody fragments, CDR region sequences set out in FIG. 1 and in SEQ ID NO:s 1-8 and 11-12, such that a particular codon is changed to a codon which codes for a different amino acid. Such a mutation is generally made by making the fewest nucleotide changes possible. A substitution mutation of this sort can be made to change an amino acid in the resulting protein in a non-conservative manner (for example, by changing the codon from an amino acid belonging to a grouping of amino acids having a particular size or characteristic to an amino acid belonging to another grouping) or in a conservative manner (for example, by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:

Amino Acids with Nonpolar R Groups
Alanine, Valine, Leucine, Isoleucine, Proline, Phenylalanine, Tryptophan, Methionine
Amino Acids with Uncharged Polar R Groups
Glycine, Serine, Threonine, Cysteine, Tyrosine, Asparagine, Glutamine
Amino Acids with Charged Polar R Groups (Negatively Charged at Ph 6.0)
Aspartic acid, Glutamic acid
Basic Amino Acids (Positively Charged at pH 6.0)
Lysine, Arginine, Histidine (at pH 6.0)

Another grouping may be those amino acids with phenyl groups:
Phenylalanine, Tryptophan, Tyrosine Another grouping may be according to molecular weight (i.e., size of R groups):

| | | | |
|---|---|---|---|
| Glycine | 75 | Alanine | 89 |
| Serine | 105 | Proline | 115 |
| Valine | 117 | Threonine | 119 |
| Cysteine | 121 | Leucine | 131 |
| Isoleucine | 131 | Asparagine | 132 |
| Aspartic acid | 133 | Glutamine | 146 |
| Lysine | 146 | Glutamic acid | 147 |
| Methionine | 149 | Histidine (at pH 6.0) | 155 |
| Phenylalanine | 165 | Arginine | 174 |
| Tyrosine | 181 | Tryptophan | 204 |

Particularly preferred substitutions are:
Lys for Arg and vice versa such that a positive charge may be maintained;
Glu for Asp and vice versa such that a negative charge may be maintained;

Ser for Thr such that a free —OH can be maintained; and Gln for Asn such that a free $NH_2$ can be maintained.

Exemplary and preferred conservative amino acid substitutions include any of: glutamine (Q) for glutamic acid (E) and vice versa; leucine (L) for valine (V) and vice versa; serine (S) for threonine (T) and vice versa; isoleucine (I) for valine (V) and vice versa; lysine (K) for glutamine (Q) and vice versa; isoleucine (I) for methionine (M) and vice versa; serine (S) for asparagine (N) and vice versa; leucine (L) for methionine (M) and vice versa; lysine (L) for glutamic acid (E) and vice versa; alanine (A) for serine (S) and vice versa; tyrosine (Y) for phenylalanine (F) and vice versa; glutamic acid (E) for aspartic acid (D) and vice versa; leucine (L) for isoleucine (I) and vice versa; lysine (K) for arginine (R) and vice versa.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces □β-turns in the protein's structure.

Two amino acid sequences are "substantially homologous" when at least about 70% of the amino acid residues (preferably at least about 80%, and most preferably at least about 90 or 95%) are identical, or represent conservative substitutions. The CDR regions of two antibodies are substantially homologous when one or more amino acids are substituted with a similar or conservative amino acid substitution, and wherein the antibody/antibodies have the profile of binding and activities of one or more of the antibodies, particularly antibody 13A1 disclosed herein. An antibody may be substantially homologous wherein one, two or three amino acids, or up to three amino acids, in the CDR domain regions are substituted with another amino acid and wherein the antibody retains the profile of antibody binding and activities.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$ with washes of higher stringency, if desired.

The term 'agent' means any molecule, including polypeptides, antibodies, polynucleotides, chemical compounds and small molecules. In particular the term agent includes compounds such as test compounds or drug candidate compounds.

The term 'agonist' refers to a ligand that stimulates the receptor the ligand binds to in the broadest sense.

The term 'assay' means any process used to measure a specific property of a compound. A 'screening assay' means a process used to characterize or select compounds based upon their activity from a collection of compounds.

The term 'preventing' or 'prevention' refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term 'prophylaxis' is related to and encompassed in the term 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Therapeutically effective amount' means that amount of a drug, compound, antimicrobial, antibody, or pharmaceutical agent that will elicit the biological or medical response of a subject that is being sought by a medical doctor or other clinician. In particular, with regard to gram-positive bacterial infections and growth of gram-positive bacteria, the term "effective amount" is intended to include an effective amount of a compound or agent that will bring about a biologically meaningful decrease in the amount of or extent of tumor regression and or increase in length of a subject's survival or period disease-free or in remission. The phrase "therapeutically effective amount" is used herein to mean an amount sufficient to prevent, and preferably reduce by at least about 30 percent, more preferably by at least 50 percent, most preferably by at least 90 percent, a clinically significant change in the growth or amount of tumor size, or enhanced survival or disease-free period by at least about 30 percent, more preferably by at least 50 percent, most preferably by at least 90 percent.

The term 'treating' or 'treatment' of any disease or infection refers, in one embodiment, to ameliorating the disease or infection (i.e., arresting the disease or growth of the infectious agent or bacteria or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or infection, either physically, (e.g., stabilization of a discernible symptom), physiologically, (e.g., stabilization of a physical parameter), or both. In a further embodiment, 'treating' or 'treatment' relates to slowing the progression of a disease or reducing an infection.

The phrase "pharmaceutically acceptable" refers to molecular entities and compositions that are physiologically tolerable and do not typically produce an allergic or similar untoward reaction, such as gastric upset, dizziness and the like, when administered to a human.

As used herein, "pg" means picogram, "ng" means nanogram, "ug" or "µg" mean microgram, "mg" means milligram, "ul" or "µl" mean microliter, "ml" means milliliter, "l" means liter.

B. DETAILED DISCLOSURE

The invention provides antibodies directed against transforming growth factor beta 1 (TGF-β1) for diagnostic and therapeutic purposes. In particular, antibodies specific for TGF-β1 are provided, wherein said antibodies recognize and are capable of binding human and mouse TGF-β1, and do not recognize or bind other TGF beta forms, particularly the antibodies do not recognize or bind TGF-β2 or TGF-β3. Exemplary TGF-β1 antibodies are particularly provided herein. Exemplary antibodies include antibodies 4C3.7, 8D6, 19D8, 4A11, 19H11, 21C11, 13A1 and 4G9. The invention particularly provides an antibody or active fragment thereof that recognizes and neutralizes TGF-β1. Exemplary antibodies capable of specifically recognizing TGF-β1 and neutralizing TGF-β1 include antibodies 4C3.7, 19D8, 13A1 and 4G9. The antibodies of the present invention have diagnostic and therapeutic use in immune modulation and cancer. In a particular aspect the antibodies of the invention are applicable in cancers, including but not limited to adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

In a general aspect, the present invention provides TGF-β1 antibodies directed against human and mouse TGF-β1, which do not cross react with or bind to TGF-β2 and/or TGF-β3 and which specifically neutralize TGF-β1 activity. In a particular spect, antibody of the present invention blocks TGF-β1-mediated signaling and/or TGF-β1 mediated cell response or cell proliferation. In a particular aspect, the invention provides anti-TGF-β1 specific antibody 13A1. In a further particular aspect the invention provides TGF-β1 specific antibody capable of specifically binding and neutralizing TGF-β1 comprising the heavy chain amino acid sequence as set out in FIG. 1. In one such aspect, the invention provides a TGF-β1 antibody comprising the heavy chain variable region CDR sequences set out in FIG. 1. In an aspect thereof TGF-β1 specific antibody is provided having a heavy chain variable region comprising the CDR 1, CDR2 and CDR3 domain amino acid sequences of GYTFTNYWMH (SEQ ID NO: 3), TIYPGNSDTN (SEQ ID NO: 4) and EDSRSLYYNGWDYFDY (SEQ ID NO:5) respectively. In an aspect, the TGF-β1 specific antibody is provided having a heavy chain variable region comprising the CDR 1, CDR2 and CDR3 domain amino acid sequences of GYTFTNYW (SEQ ID NO: 11), IYPGNSDT (SEQ ID NO: 12) and EDSRSLYYNGWDYFDY (SEQ ID NO: 5) respectively, wherein a shorter accepted CDR1 and CDR2 domain amino acid sequence is specified. The antibody of the invention may comprise the heavy chain variable region amino acid sequence (SEQ ID NO: 1) set out in FIG. 1 or the heavy chain CDR domain region CDR1, CDR2 and CDR3 sequences of FIG. 1, and a light chain variable region. The antibody of the invention may comprise the light chain variable region amino acid sequence (SEQ ID NO: 2) or the light chain CDR sequences as set out in FIG. 1. In an aspect thereof TGF-β1 specific antibody is provided having a light chain variable region comprising the CDR 1, CDR2 and CDR3 domain amino acid sequences of ESVDNYGISF (SEQ ID NO: 6), YAAS (SEQ ID NO: 7) and QQSKEVPRT (SEQ ID NO: 8) respectively.

Panels of monoclonal antibodies recognizing human and murine TGF-β1 can be screened for various properties; i.e., isotype, epitope, affinity, etc. Of particular interest are antibodies that mimic the activity of exemplary antibodies 4C3.7, 19D8, 13A1 and/or 4G9, and have affinity for human and mouse TGF-β1, do not react with TGF-β2 or TGF-β3, and directly affect the activity of TGF-β1, in particular neutralize TGF-β1. Such antibodies can be readily identified and/or screened in specific binding member activity assays.

A monoclonal antibody of the present invention may comprise heavy chain variable region, such as exemplified in FIG. 1, and optionally light chain variable region. In general, the CDR regions, comprising amino acid sequences substantially as set out as the CDR regions of FIG. 1 will be carried in a structure which allows for binding of the CDR regions to the TGF-β1, and particularly to human and mouse TGF-β1.

By "substantially as set out" it is meant that that variable region sequences, and/or particularly the CDR sequences, of the invention will be either identical or highly homologous to the specified regions of FIG. 1. By "highly homologous" it is contemplated that only a few substitutions, preferably from 1 to 8, preferably from 1 to 5, preferably from 1 to 4, or from 1 to 3, or 1 or 2 substitutions may be made in the variable region sequence and/or in the CDR sequences. The term substantially set out as includes particularly conservative amino acid substitutions which do not materially or significantly affect the specificity and/or activity of the instant antibodies. Conservative and non-conservative amino acid substitutions are contemplated herein for the variable region sequences and also for the CDR region sequences.

Substitutions may be made in the variable region sequence outside of the CDRs so as to retain the CDR sequences. Thus, changes in the variable region sequence or alternative non-homologous or veneered variable region sequences may be introduced or utilized, such that the CDR sequences are maintained and the remainder of the variable region sequence may be substituted.

Alternatively, substitutions may be made particularly in the CDRs. CDR sequences for the antibody, particularly antibody 13A1, of the present invention are set out and described herein including in FIG. 1. Antibody 13A1 comprises heavy chain CDR sequences CDR1 GYTFTNYWMH (SEQ ID NO: 3), CDR2 TIYPGNSDTN (SEQ ID NO: 4) and CDR3 EDSRSLYYNGWDYFDY (SEQ ID NO: 5), as set out in FIG. 1. When specifying a shorter accepted set of CDRs, the antibody comprises heavy chain CDR sequences CDR1 GYTFTNYW (SEQ ID NO: 11), CDR2 IYPGNSDT (SEQ ID NO: 12) and CDR3 EDSRSLYYNGWDYFDY (SEQ ID NO: 5). Antibody 13A1 comprises light chain CDR sequences CDR1 ESVDNYGISF (SEQ ID NO: 6), CDR2 YAAS (SEQ ID NO: 7) and CDR3 QQSKEVPRT (SEQ ID NO: 8).

Antibodies of the invention having substitutions as above described and contemplated are selected to maintain the activities and specificity commensurate with the exemplary antibodies, including antibody 13A1 and having the characteristics as set out herein and in the claims.

The structure for carrying the CDRs of the invention will generally be of an antibody heavy or light chain sequence or substantial portion thereof in which the CDR regions are located at locations corresponding to the CDR region of naturally occurring VH and VL antibody variable domains encoded by rearranged immunoglobulin genes. The structures and locations of immunoglobulin variable domains may be determined by reference to Kabat, E. A. et al, Sequences of Proteins of Immunological Interest. 4th Edition. US Department of Health and Human Services. 1987, and updates thereof, now available on the Internet (immuno.bme.nwu).

The variable domains may be derived from any germline or rearranged human variable domain, or may be a synthetic variable domain based on consensus sequences of known human variable domains. The CDR-derived sequences of the invention, as defined in the preceding paragraph, may be introduced into a repertoire of variable domains lacking CDR regions, using recombinant DNA technology.

For example, Marks et al (Bio/Technology, 1992, 10:779-783) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR/CDRs. Marks et al further describe how this repertoire may be combined with a CDR of a particular antibody. The repertoire may then be displayed in a suitable host system such as the phage display system of WO92/01047 so that suitable specific binding members may be selected. A repertoire may consist of from anything from $10^4$ individual members upwards, for example from $10^6$ to $10^8$ or $10^{10}$ members. Analogous shuffling or combinatorial techniques are also disclosed by Stemmer (Nature, 1994, 370:389-391), who describes the technique in relation to a β-lactamase gene but observes that the approach may be used for the generation of antibodies.

A further alternative is to generate novel VH or VL regions carrying the CDR-derived sequences of the invention using random mutagenesis of, for example, the Ab VH or VL genes to generate mutations within the entire variable domain. Such a technique is described by Gram et al (1992, Proc. Natl. Acad. Sci., USA, 89:3576-3580), who used error-prone PCR. Another method which may be used is to direct mutagenesis to CDR regions of VH or VL genes. Such techniques are disclosed by Barbas et al, (1994, Proc. Natl. Acad. Sci., USA, 91:3809-3813) and Schier et al (1996, J. Mol. Biol. 263:551-567).

All the above described techniques are known as such in the art and in themselves do not form part of the present invention. The skilled person will be able to use such techniques to provide specific binding members of the invention using routine methodology in the art.

A substantial portion of an immunoglobulin variable domain will comprise at least the three CDR regions, together with their intervening framework regions. Preferably, the portion will also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of specific binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including immunoglobulin heavy chains, other variable domains (for example in the production of diabodies) or protein labels as provided herein and/or known to those of skill in the art.

Although in a preferred aspect of the invention specific binding members comprising a pair of binding domains based on sequences substantially set out in FIG. 1 are preferred, single binding domains based on either of these sequences, particularly based on the heavy chain and heavy chain CDRs, form further aspects of the invention. In the case of the binding domains based on the sequence substantially set out in FIG. 1, such binding domains may be used as targeting agents for TGF-β1, since it is known that immunoglobulin VH domains are capable of binding target antigens in a specific manner.

This may be achieved by phage display screening methods using the so-called hierarchical dual combinatorial approach as disclosed in U.S. Pat. No. 5,969,108 in which an individual colony containing either an H or L chain clone is used to infect a complete library of clones encoding the other chain (L or H) and the resulting two-chain specific binding member is selected in accordance with phage display techniques such as those described in that reference. This technique is also disclosed in Marks et al, ibid. Phage library and phage display selection systems and techniques are also provided herein.

Portions or domains of the antibodies of the invention are contemplated and incorporated, including any portion or domain, including those modified or fused to reagents, labels or other domains or fragments, wherein the portions or domains retain the characteristics of the antibodies hereof, including TGF-β1 specific binding, and optionally including TGF-β1 specific neutralization, as exemplified in antibody 13A1 hereof Antibodies and antibody fragments of the invention include smaller recombinant antibody fragments (for example, classic monovalent antibody fragments (Fab, scFv) and engineered variants (diabodies, triabodies, minibodies and single-domain antibodies) that retain the targeting specificity of the whole antibodies (mAbs) (for review see Hollinger P and Hudson P J (2005) Nature Biotech 23(9):1126-1136). These include for example domain antibody (dAb) fragment, which comprises a single variable domain (Ward, E. S. et al., Nature 341, 544-546 (1989)); camelid antibody; isolated complementarity determining region (CDR); Single Chain Fv Fragments wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); a diabody, which is a bivalent, bispecific antibody in which VH and VL domains are expressed on a single polypeptide chain, but using a linker that is too short to allow for pairing between the two domains on the same chain, thereby forcing the domains to pair with the complementarity domains of another chain and creating two antigen binding sites (WO94/13804; P. Holliger et al Proc. Natl. Acad. Sci. USA 90 6444-6448, (1993)); a linear antibody, which comprises a pair of tandem Fv segments (VH-CH1-VH-CH1) which, together with complementarity light chain polypeptides, form a pair of antigen binding regions; multivalent antibody fragments (scFv dimers, trimers and/or tetramers (Power and Hudson, J Immunol. Methods 242: 193-204 9 (2000)); and minibody, which is a bivalent molecule comprised of scFv fused to constant immunoglobulin domains, CH3 or CH4 (for example IgG1 ($C_H3$) and IgE ($C_H4$)), wherein the constant CH3 or CH4 domains serve as dimerization domains (Olafsen T et al (2004) Prot Eng Des Sel 17(4): 315-323; Hollinger P and Hudson P J (2005) Nature Biotech 23(9):1126-1136). These smaller antibodies and engineered variants or fragments can be produced more economically and may possess other unique and superior properties for a range of diagnostic and therapeutic applications. For example, scFV2-Fc can accumulate in higher abundance in tumor or tissue, and a minibody is approximately 80 kD and may be ideal for therapy because of higher uptake in tissues, have faster clearance and have better tissue to blood ratios than intact immunoglobulin (150 kDa) or Fab'2 (110 kDa). The antibody fragments may be forged into multivalent and multispecific reagents, linked to therapeutic payloads (such as radionuclides, toxins, enzymes, liposomes and viruses) and engineered for enhanced therapeutic efficacy. Recently, single antibody domains have been engineered and selected as targeting reagents against hitherto immunosilent cavities in enzymes, receptors and infectious agents.

Specific binding members of the present invention may further comprise antibody constant regions or parts thereof. For example, specific binding members based on the sequences of FIG. 1 may be attached at their C-terminal end to antibody light chain constant domains including human Cκ or Cλ chains, preferably Cλ chains. Similarly, specific binding members based on the sequences of FIG. 1 may be attached at their C-terminal end to all or part of an immunoglobulin heavy chain derived from any antibody isotype, e.g. IgG, IgA, IgE, IgD and IgM and any of the isotype sub-classes, particularly IgG1, IgG2b, and IgG4. IgG1 is preferred.

The antibodies, or any fragments thereof, may be conjugated or recombinantly fused to any cellular toxin, bacterial or other, e.g. *pseudomonas* exotoxin, ricin, or diphtheria toxin. The part of the toxin used can be the whole toxin, or any particular domain of the toxin. Such antibody-toxin molecules have successfully been used for targeting and therapy of different kinds of cancers, see e.g. Pastan, Biochim Biophys Acta. 1997 Oct. 24; 1333(2):C1-6; Kreitman et al., N Engl J Med. 2001 Jul. 26; 345(4):241-7; Schnell et al., Leukemia. 2000 January; 14(1):129-35; Ghetie et al., Mol Biotechnol. 2001 July; 18(3):251-68.

Bi- and tri-specific multimers can be formed by association of different scFv molecules and have been designed as cross-linking reagents for T-cell recruitment into tumors (immunotherapy), viral retargeting (gene therapy) and as red blood cell agglutination reagents (immunodiagnostics), see e.g. Todorovska et al., J Immunol Methods. 2001 Feb. 1; 248(1-2):47-66; Tomlinson et al., Methods Enzymol. 2000; 326:461-79; McCall et al., J Immunol. 2001 May 15; 166(10):6112-7.

Fully human antibodies can be prepared by immunizing transgenic mice carrying large portions of the human immunoglobulin heavy and light chains. These mice, examples of such mice are the Xenomouse™ (Abgenix, Inc.) (U.S. Pat. Nos. 6,075,181 and 6,150,584), the HuMAb-Mouse™ (Medarex, Inc./GenPharm) (U.S. Pat. Nos. 5,545,806 and 5,569,825), the TransChromo Mouse™ (Kirin) and the KM Mouse™ (Medarex/Kirin), are well known within the art. Antibodies can then be prepared by, e.g. standard hybridoma technique or by phage display. These antibodies will then contain only fully human amino acid sequences. Fully human antibodies can also be generated using phage display from human libraries. Phage display may be performed using methods well known to the skilled artisan, and as provided herein as in Hoogenboom et al and Marks et al (Hoogenboom H R and Winter G. (1992) J Mol Biol.

227(2):381-8; Marks J D et al (1991) J Mol Biol. 222(3): 581-97; and also U.S. Pat. Nos. 5,885,793 and 5,969,108).

Antibodies of the invention may be labelled with a detectable or functional label. Detectable labels include, but are not limited to, radiolabels such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{121}$I, $^{124}$I, $^{125}$I, $^{131}$I, $^{111}$In, $^{117}$Lu, $^{211}$At, $^{198}$Au, $^{67}$Cu, $^{225}$Ac, $^{213}$Bi, $^{99}$Tc and $^{186}$Re, which may be attached to antibodies of the invention using conventional chemistry known in the art of antibody imaging. Labels also include fluorescent labels (for example fluorescein, rhodamine, Texas Red) and labels used conventionally in the art for MRI-CT imaging. They also include enzyme labels such as horseradish peroxidase, β-glucoronidase, β-galactosidase, urease. Labels further include chemical moieties such as biotin which may be detected via binding to a specific cognate detectable moiety, e.g. labelled avidin. Functional labels include substances which are designed to be targeted to the site of a tumor to cause destruction of tumor tissue. Such functional labels include cytotoxic drugs such as 5-fluorouracil or ricin and enzymes such as bacterial carboxypeptidase or nitroreductase, which are capable of converting prodrugs into active drugs at the site of a tumor.

TGF-β1 plays an important role in controlling the immune system and is a tumor promoter and a tumor suppressor. Studies of TGF-β in cancer provide a rational for blocking TGF-β signaling in human cancers for therapeutic effect. Overexpression of TGF-β ligands have been reported in most cancers, including in tumors resistant to conventional chemotherapy, and high levels of these in tumor tissues and/or serum are associated with early metastatic recurrences and/or poor patient outcome (Teicher, B. A. et al (1997) In Vivo 11:463-472; Wojtowicz-Praga, S. (2003) Invest New Drugs 21:21-32; Ito, N., et al. (1995) Cancer Lett 89:45-48; Shariat, S. F., et al (2001) Cancer 92:2985-2992; Shariat, S. F., et al (2001) J Clin Oncol 19:2856-2864; Tsushima, H., et al (2001) Clin Cancer Res 7:1258-1262; Rich, J. N. (2003) Front Biosci 8:e245-e260). Animal studies with pan-TGF-β antibody have shown inhibition of tumor recurrence or metastasis in fibrosarcoma, colon cancer, and breast cancer (Terabe M et al (2003) J Exp Med 198:1741-1752; Nam J-S et al (2008) Cancer Res 68(10): 3835-3843), and reduced radiation-induced acceleration of metastatic breast cancer (Biswas S et al (2007) 117:1305-1313). Evidence to date strongly supports that blocking TGFβ can enhance antigen uptake, presentation, and activation of antitumor immune response mediated by therapeutic vaccines. Indeed, recent studies have demonstrated that blockade of TGF-β, using mouse TGF-β generic antibody ID11 (which recognizes TGF-β1, TGF-β2 and TGF-β3), synergistically enhances tumor vaccines in animal models via CD8$^+$ T cells (Terabe M et al (2009) Clin Cancer Res 15:6560-6569; Takaku S et al (2010) Int J Cancer 126(7):1666).

It is notable that in radiation studies, thoracic radiation and chemotherapy in metastatic breast cancer models specifically induced plasma TGF-β1 levels (Biswas S et al (2007) 117:1305-1313), and that generic blockade of TGF-β response in mice inhibited prostate cancer metastasis, but led to widespread inflammatory disease in the animals (Shah A H, et al (2002) J Immunol 169:3485-91). Therefore, availability of a TGF-β1 specific inhibitor, particularly a TGF-β1 specific antibody, can provide more directed and targeted intervention and control of immune response and cancer modulation, without such risk of widespread inflammatory disease or off-target effects in an animal or patient.

TGF-β antibodies have been generated and a particular example denoted 1D11, and its humanized counterpart GC1008, have been evaluated in animal models and early human clinical trials and are provided and disclosed in patent applications including in WO2007076391, WO2005097832, WO2006086469 and U.S. Pat. No. 5,571,714. Antibody 1D11 and its humanized counterpart, however, are generic TGF-beta antibodies, recognizing all TGF-β forms including TGF-β1, TGF-β2 and TGF-β3. Antibody 1D11 and its humanized counterpart do not, therefore, provide specific and directed modulation of TGF-β1. TGF-β1 specific antibodies are disclosed in WO2006116002 and WO2000066631 but are distinct from any exemplary antibodies described herein.

Monocolonal antibodies derived by hybridoma technique from another species than human, such as mouse, can be humanized, which means that a non-human antibody is genetically engineered to be more human in order to avoid HAMA when infused into humans. The methods humanization of antibodies are well known within the art, among the more more common methods are complementarity-determining region (CDR) grafting and veneering (also known as resurfacing). These methods have been extensively described in the literature and in patents, see e.g.; King "Applications and Engineering of Monoclonal Antibodies" Taylor & Francis, 1998; U.S. Pat. Nos. 5,225,539; 5,530,101; 5,585,089, 5,859,205 and 6,797,492, each incorporated herein by reference. Another common method is the veneering (v) technology (Daugherty et al. (1991). Nucleic Acids Res. 19(9), 2471-6; U.S. Pat. No. 6,797,492; Padlan, E. A. (1991) Mol. Immunol. 28(4-5), 489-98; European Patent No. 519596). Where a replacement of the surface-exposed residues in the framework regions, which differ from those usually found in human antibodies, is performed in order to minimize the immunogenicity of an antibody's variable domains, while preserving ligand-binding properties.

Antibodies including fragments thereof, and drugs that modulate the production or activity of the specific binding members, antibodies and/or their subunits may possess certain diagnostic applications and may for example, be utilized for the purpose of detecting and/or measuring conditions such as cancer, precancerous lesions, conditions related to or resulting from hyperproliferative cell growth or the like. For example, the specific binding members, antibodies or their subunits may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the specific binding members of the invention may be discovered or synthesized, and may be used in diagnostic and/or therapeutic protocols.

The radiolabelled specific binding members, particularly antibodies and fragments thereof, are useful in in vitro diagnostics techniques and in in vivo radioimaging techniques and in radioimmunotherapy. In the instance of in vivo imaging, the specific binding members of the present invention may be conjugated to an imaging agent rather than a radioisotope(s), including but not limited to a magnetic resonance image enhancing agent, wherein for instance an antibody molecule is loaded with a large number of paramagnetic ions through chelating groups. Examples of chelating groups include EDTA, porphyrins, polyamines crown ethers and polyoximes. Examples of paramagnetic ions include gadolinium, iron, manganese, rhenium, europium, lanthanium, holmium and ferbium. In a further aspect of the invention, radiolabelled specific binding members, particularly antibodies and fragments thereof, particularly radioimmunoconjugates, are useful in radioimmunotherapy, particularly as radiolabelled antibodies for cancer therapy. In a still further aspect, the radiolabelled specific binding members, particularly antibodies and fragments thereof, are useful in radioimmuno-guided surgery techniques, wherein they can identify and indicate the presence and/or location of cancer cells, precancerous cells, tumor cells, and hyperproliferative cells, prior to, during or following surgery to remove such cells.

Immunoconjugates or antibody fusion proteins of the present invention, wherein the specific binding members, particularly antibodies and fragments thereof, of the present invention are conjugated or attached to other molecules or agents further include, but are not limited to binding members conjugated to a chemical ablation agent, toxin, immunomodulator, cytokine, cytotoxic agent, chemotherapeutic agent or drug.

Radioimmunotherapy (BAIT) has entered the clinic and demonstrated efficacy using various antibody immunoconjugates. $^{131}$I labeled humanized anti-carcinoembryonic antigen (anti-CEA) antibody hMN-14 has been evaluated in colorectal cancer (Behr T M et al (2002) Cancer 94(4Suppl): 1373-81) and the same antibody with $^{90}$Y label has been assessed in medullary thyroid carcinoma (Stein R et al (2002) Cancer 94(1):51-61). Radioimmunotherapy using monoclonal antibodies has also been assessed and reported for non-Hodgkin's lymphoma and pancreatic cancer (Goldenberg D M (2001) Crit Rev Oncol Hematol 39(1-2):195-201; Gold D V et al (2001) Crit Rev Oncol Hematol 39 (1-2) 147-54). Radioimmunotherapy methods with particular antibodies are also described in U.S. Pat. Nos. 6,306,393 and 6,331,175. Radioimmunoguided surgery (RIGS) has also entered the clinic and demonstrated efficacy and usefulness, including using anti-CEA antibodies and antibodies directed against tumor-associated antigens (Kim J C et al (2002) Int J Cancer 97(4):542-7; Schneebaum S et al (2001) World J Surg 25(12):1495-8; Avital S et al (2000) Cancer 89(8): 1692-8; McIntosh D G et al (1997) Cancer Biother Radiopharm 12 (4):287-94).

In vivo animal models of cancer or animal xenograft studies may be utilized by the skilled artisan to further or additionally screen, assess, and/or verify the specific binding members and antibodies or fragments thereof of the present invention, including further assessing TGF-β1 modulation and inhibition in vivo and inhibiting tumor progression, recurrence, metastasis, or immune response against tumor cells or response to antigens or vaccines, including tumor or cancer antigens or vaccines. Such animal models include, but are not limited to models of immune response, immune modulation, vaccination, cancer, cancer metastasis. Models of cancers whose recurrence or metastasis are associated with elevated levels of TGF-β1 are particularly susceptible to and targeted by the antibodies of the present invention. Such cancers include melanomas, breast, lung and prostate cancer. Exemplary and suitable models are known and readily available to the skilled artisan and include those referenced and/or described herein and known in the art. For example, antibodies or active fragments thereof of the invention may be evaluated in breast cancer models, including tumorigenicity of human breast cancer cells in athymic mice (Arteaga C L et al (1993) Cell Growth Diff 4:193-201) or in Neu-induced mammary tumors (Muraoka-Cok R S et al (2004) Cancer Res 64:2002-2011), or in evaluating metastases of transgenic mammary tumors (Siegel P M et al (2003) Proc Natl Acad Sci USA 100:8430-8435). Also, as an example the anti-tumor effect of TGF-β1 antibody can be examined on a whole cell vaccine in prophylaxis against injected CT26 colon carcinoma tumors in syngeneic mice using a method similar to that reported by Takaku et al (Takaku S et al (2010) Int J Cancer 126(7):1666).

Antibodies of the present invention may be administered to a patient in need of treatment via any suitable route, including by injection intramuscularly, subcutaneous, into the bloodstream or CSF, or directly into the site of the tumor. The precise dose will depend upon a number of factors, including whether the antibody is for diagnosis or for treatment, the size and location of the tumor, the precise nature of the antibody (whether whole antibody, fragment, diabody, etc), and the nature of the detectable or functional label attached to the antibody. Where a radionuclide is used for therapy, a suitable maximum single dose may be about 45 mCi/m$^2$, to a maximum of about 250 mCi/m$^2$. Preferable dosage is in the range of 15 to 40 mCi, with a further preferred dosage range of 20 to 30 mCi, or 10 to 30 mCi. Such therapy may require bone marrow or stem cell replacement. A typical antibody dose for either tumor imaging or tumor treatment will be in the range of from 0.5 to 40 mg, preferably from 1 to 4 mg of antibody in F(ab')2 form. Naked antibodies are preferably administered in doses of 20 to 1000 mg protein per dose, or 20 to 500 mg protein per dose, or 20 to 100 mg protein per dose. This is a dose for a single treatment of an adult patient, which may be proportionally adjusted for children and infants, and also adjusted for other antibody formats, in proportion for example to molecular weight. Treatments may be repeated at daily, twice-weekly, weekly or monthly intervals, at the discretion of the physician.

Pharmaceutical and Therapeutic Compositions

Specific binding members of the present invention will usually be administered in the form of a pharmaceutical composition, which may comprise at least one component in addition to the specific binding member. Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous, or by deposition at a tumor site.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, injection, or injection at the site of affliction, the active ingredient may be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A composition may be administered alone or in combination with other treatments, therapeutics or agents, either simultaneously or sequentially dependent upon the condition to be treated. In addition, the present invention contemplates and includes compositions comprising the binding member, particularly antibody or fragment thereof, herein described and other agents or therapeutics such as anti-cancer agents or therapeutics, hormones, anti-mitotic agents, anti-apoptotic agents, antibodies, or immune modulators. More generally these anti-cancer agents may be but are not limited to tyrosine kinase inhibitors or phosphorylation cascade inhibitors, post-translational modulators, cell growth or division inhibitors (e.g. anti-mitotics), or signal transduction inhibitors. Other treatments or therapeutics may include the administration of suitable doses of pain relief drugs such as non-steroidal anti-inflammatory drugs (e.g. aspirin, paracetamol, ibuprofen or ketoprofen) or opiates such as morphine, or anti-emetics. The composition can be administered in combination (either sequentially (i.e. before or after) or simultaneously) with tyrosine kinase inhibitors (including, but not limited to AG1478 and ZD1839, STI571, OSI-774, SU-6668), doxorubicin, temozolomide, cisplatin, carboplatin, nitrosoureas, procarbazine, vincristine, hydroxyurea, 5-fluoruracil, cytosine arabinoside, cyclophosphamide, epipodophyllotoxin, carmustine, lomustine, and/or other chemotherapeutic agents. Thus, these agents may be specific anti-cancer agents, or immune cell response modulators or may be more general anti-cancer and anti-neoplastic agents such as doxorubicin, cisplatin, temozolomide, nitrosoureas, procarbazine, vincristine, hydroxyurea, 5-fluoruracil, cytosine arabinoside, cyclophosphamide, epipodophyllotoxin, carmustine, or lomustine. In addition, the composition may be administered with hormones such as dexamethasone, immune modulators, such as interleukins, tumor necrosis factor (TNF) or other growth factors, colony stimulating factors, cytokines, agonist or antagonist antibodies to regulators of immune response which stimulate, enhance, or derepress the immune response and reduction or elimination of cancer cells or tumors. The composition may also be administered with, or may include combinations along with other anti-tumor antigen antibodies.

In addition, the present invention contemplates and includes therapeutic compositions for the use of the binding member in combination with conventional radiotherapy.

The present invention further contemplates therapeutic compositions useful in practicing the therapeutic methods of this invention. A subject therapeutic composition includes, in admixture, a pharmaceutically acceptable excipient (carrier) and one or more of a specific binding member, polypeptide analog thereof or fragment thereof, as described herein as an active ingredient. In a preferred embodiment, the composition comprises an antigen capable of modulating the specific binding of the present binding member/antibody with a target cell. In an embodiment the composition comprises an antigen or vaccine formulation, particularly a tumor antigen or cancer vaccine.

The preparation of therapeutic compositions which contain polypeptides, analogs or active fragments as active ingredients is well understood in the art. Typically, such compositions are prepared as injectables, either as liquid solutions or suspensions. However, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic antibody- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of peptide/MHC or tumor antigen binding capacity desired. Precise amounts of active ingredient required to be administered depend on the judgment of the practitioner and are peculiar to each individual. Suitable regimes for initial administration and follow on administration are also variable, and may include an initial administration followed by repeated doses at one or more hour intervals by a subsequent injection or other administration. Alternatively, continuous intravenous infusion sufficient to maintain appropriate and sufficient concentrations in the blood or at the site of desired therapy is contemplated.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Diagnostic Assays

The present invention also relates to a variety of diagnostic applications, including methods for detecting the expression of or elevated presence of TGF-β1, TGF-β1-mediated cancer, or cancer more generally, evaluating the presence or amount of TGF-β1-responsive cells, by reference to their ability to be recognized by the present specific binding member(s). Peptide complexes can be identified, targeted, labeled, and/or quantitated on cells, including immune cells and/or tumor cells.

Diagnostic applications of the specific binding members of the present invention, particularly antibodies and fragments thereof, include in vitro and in vivo applications well known and standard to the skilled artisan and based on the present description. Diagnostic assays and kits for in vitro assessment and evaluation of tumor and cancer status, and tumor response or immune response, may be utilized to diagnose, evaluate and monitor patient samples including those known to have or suspected of having cancer, a precancerous condition, a condition related to hyperproliferative cell growth or from a tumor sample. The assessment and evaluation of cancer, tumor and metastatic disease status is also useful in determining the suitability of a patient for a clinical trial of a drug or for the administration of a particular chemotherapeutic agent or specific binding member, particularly an antibody, of the present invention, including combinations thereof, versus a different agent or binding member. This type of diagnostic monitoring and assessment is already in practice utilizing antibodies against the HER2 protein in breast cancer (HERCEPTEST, Dako Corporation), where the assay is also used to evaluate patients for antibody therapy using Herceptin. In vivo applications include imaging of tumors or assessing cancer status of individuals, including radioimaging.

Preferably, the antibody used in the diagnostic methods of this invention is mouse, human, humanized or recombinant antibody. More preferably, the antibody is a single chain chain antibody or domain antibody. In addition, the antibody molecules used herein can be in the form of Fab, Fab', F(ab')$_2$ or F(v) portions of whole antibody molecules, particularly Fab.

The presence of TGF-β1 in cells or TGF-β1 responsive cells or TGF-β1 responsive genes or proteins can be ascertained by the usual in vitro or in vivo immunological procedures applicable to such determinations. A number of useful procedures are known. The procedures and their application are all familiar to those skilled in the art and accordingly may be utilized within the scope of the present invention. The "competitive" procedure is described in U.S. Pat. Nos. 3,654,090 and 3,850,752. The "sandwich" procedure, is described in U.S. Pat. Nos. RE 31,006 and 4,016,043. Still other procedures are known such as the "double antibody," or "DASP" procedure.

In a further embodiment of this invention, commercial test kits suitable for use by a medical specialist may be prepared to determine the presence or absence of aberrant expression of including but not limited to amplified TGF-β1, in suspected target cells. In accordance with the testing techniques discussed above, one class of such kits will contain at least the labeled or its binding partner, for instance an antibody specific thereto, and directions, of course, depending upon the method selected, e.g., "competitive," "sandwich," "DASP" and the like. The kits may also contain peripheral reagents such as buffers, stabilizers, etc.

Accordingly, a test kit may be prepared for the demonstration of the presence of or elevated levels of TGF-β1 or a TGF-β1-responsive element or protein, comprising:
(a) a predetermined amount of at least one labeled immunochemically reactive component obtained by the direct or indirect attachment of the present specific binding member or a specific binding partner thereto, to a detectable label;
(b) other reagents; and
(c) directions for use of said kit.

A test kit may be prepared for the demonstration of the presence of TGF-β1-mediated cancer, particularly selected from breast, lung, liver, prostate, bladder cancer comprising:
(a) a predetermined amount of at least one labeled immunochemically reactive component obtained by the direct or indirect attachment of the present specific binding member or a specific binding partner thereto, to a detectable label;
(b) other reagents; and
(c) directions for use of said kit.

In accordance with the above, an assay system for screening potential drugs effective to modulate the presence or activity of TGF-β1 and/or the activity or binding of the antibody of the present invention may be prepared. The antigen peptide or the binding member or antibody may be introduced into a test system, and the prospective drug may also be introduced into the resulting cell culture, and the culture thereafter examined to observe any changes in the activity of the cells, binding of the antibody, or amount and extent of TGF-β1 due either to the addition of the prospective drug alone, or due to the effect of added quantities of the known agent(s).

Nucleic Acids

The present invention further provides an isolated nucleic acid encoding a specific binding member of the present invention. Nucleic acid includes DNA and RNA. In a preferred aspect, the present invention provides a nucleic acid which codes for a polypeptide of the invention as defined above, including a polypeptide as set out in FIG. 1 or capable of encoding the CDR regions thereof.

The present invention also provides constructs in the form of plasmids, vectors, transcription or expression cassettes which comprise at least one polynucleotide as above. The present invention also provides a recombinant host cell which comprises one or more constructs as above. A nucleic acid encoding any specific binding member as provided itself forms an aspect of the present invention, as does a method of production of the specific binding member which method comprises expression from encoding nucleic acid therefor. Expression may conveniently be achieved by culturing under appropriate conditions recombinant host cells containing the nucleic acid. Following production by expression a specific binding member may be isolated and/or purified using any suitable technique, then used as appropriate.

Specific binding members and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes origin other than the sequence encoding a polypeptide with the required function. Nucleic acid according to the present invention may comprise DNA or RNA and may be wholly or partially synthetic.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, cancer cells, ovarian cancer cells and many others. A common, preferred bacterial host is *E. coli*. The expression of antibodies and antibody fragments in prokaryotic cells such as *E. coli* is well established in the art.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. eds., John Wiley & Sons, 1992. The disclosures of Sambrook et al. and Ausubel et al. are incorporated herein by reference.

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene. The present invention also provides a method which comprises using a construct as stated above in an expression system in order to express a specific binding member or polypeptide as above.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host. A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col El, pCR1, pBR322, pMB9 and their derivatives, plasmids such as RP4; phage DNAs, e.g., the numerous derivatives of phage λ, e.g., NM989, and other phage DNA, e.g., M13 and filamentous single stranded phage DNA; yeast plasmids such as the 2 u plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast □-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli, Pseudomonas, Bacillus, Streptomyces*, fungi such as yeasts, and animal cells, such as CHO, YB/20, NSO, SP2/0, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products. Considering these and other factors a person skilled in the art will be able to construct a variety of vector/expression control sequence/host combinations that will express the DNA sequences of this invention on fermentation or in large scale animal culture.

As mentioned above, a DNA sequence encoding a specific binding member can be prepared synthetically rather than cloned. The DNA sequence can be designed with the appropriate codons for the specific binding member amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, *Nature*, 292:756 (1981); Nambair et al., *Science*, 223:1299 (1984); Jay et al., *J. Biol. Chem.*, 259:6311 (1984). Synthetic DNA sequences allow convenient construction of genes which will express specific binding member analogs or "muteins". Alternatively, DNA encoding muteins can be made by site-directed mutagenesis of native specific binding member genes or cDNAs, and muteins can be made directly using conventional polypeptide synthesis.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

Example 1

Production of TGFbeta-1 Antibodies

TGF-beta antibodies were generated using a procedure in mice we have termed 'auto-vaccination'. Auto-vaccination was successfully utilized to generate antibodies in mice against several proteins involved in the control of immune and inflammatory responses. In this procedure, large OVA multimers were made by treating ovalbumin (OVA) with glutaraldehyde to generate OVAglu and, after purifying the polymerized products by size exclusion chromatography, these OVA multimers are reacted with the target cytokine (in this instance TGF-beta1) before saturating remaining glutaraldehyde sites with PADRE peptide (aKXVAAWTLKAAC) (SEQ ID NO: 9) (Alexander, J. et al (1994) Immunity 1:751-761) to maximize immunogenicity. The efficacy of OVAglu in breaking tolerance against self-antigens was demonstrated by detection of specific antibodies to TGF-beta 1 by ELISA at serum dilutions of $10^4$-$10^6$.

Antibodies to human TGF-beta-1 were prepared by subcutaneous vaccination of C57BL/6 mice in the footpads with 2-5 ug of human TGF-beta1-OVA-PADRE complexes along with GERBU100 adjuvant 5 times at 2 week intervals. Mice were bled two weeks after the last boost. After a 2 to 6 week rest, a combined intravenous and intraperitoneal booster with 2-5 ug complexes was given for mAb production.

TGF-beta1-OVA-PADRE complex was generated by coupling of human TGF-beta-1 cytokine with amine-reactive ovalbumin polymers by incubation with stirring at 4° C. with an equimolar amount of target protein at pH 8.5 and 0.1M carbonate buffer to deprotonate amino groups of the cytokine and allow their reaction with free glutaraldehyde components. After 6 h at room temperature followed by overnight at 4° C., Tetanus Toxin peptide (CQYIKANSKFIGITEL) (SEQ ID NO: 10) was added. Following additional 6 to 12 h incubation, a tenfold molar excess of PADRE peptide (aKXVAAWTLKAAC) was added, and the mixture was incubated further overnight before dialysis against 0.1 M glycine buffer, pH 5.8. In the PADRE sequence X=cycloexylamin, a=D amino acid.

A group of mouse TGF-β1 antibodies were isolated: MTGF-beta-1.4C3.7 (also denoted Ab 4C3.7), MTGF-beta1.8D6 (also denoted antibody 8D6), MTGF-beta-1.19D8 (also denoted antibody 19D8), MTGF-beta-1.4A11 (also denoted antibody 4A11), MTGF-beta-1.19H11 (also denoted antibody 19H11), MTGF-beta-1.21C11 (also denoted antibody 21C11), MTGF-beta1.13A1 (also denoted antibody 13A1) and MTGF-beta 1.4G9 (also denoted antibody 4G9). The antibodies are all IgG class antibodies, and differ in subclass. Antibodies 4C3.7, 8D6, 19D8 and 13A11 are IgG1. Antibodies 4A11 and 4G9 are IgG2b. Antibodies 19H11 and 21C11 are IgG2a. The antibodies were subsequently evaluated for TGFβ1 binding and TGF-β1 neutralization as described in the next Examples.

Materials and Methods
Reagents and Mice

All vaccinations were performed in C57BL/6 mice maintained under specific pathogen-free conditions at our animal facility (Ludwig Institute for Cancer Research, Brussels Branch, Brussels, Belgium). Human TGF-β1, which differs from the mouse mature protein by a single amino acid (A in man and S in mouse at position 354) (Derynck R et al (1986) J Biol Chem 261:4377-4379), was from R&D Systems or was produced and purified by Dr. Peter Sun (Structural Immunology Section, Lab of Immunogenetics, National Institute of Allergy and Infectious Diseases/National Institutes of Health, Bethesda, Md., USA).

Activated Carrier Production

OVA (Product A2512, Sigma-Aldrich, St. Louis, Mo., USA), at a concentration of 0.22 mM, was polymerized by overnight incubation with 20 mM glutaraldehyde in 50 mM potassium phosphate buffer, pH 6, at 4° C. After dialysis against the same buffer, the soluble product was fractionated on a SUPEROSE12 size exclusion column (GE Healthcare, Diegem, Belgium), equilibrated at pH 6 in 50 mM phosphate buffer. Large size products (>1000 kD), hereafter designated OVAglu, were collected and frozen at −80° C. in aliquots.

Coupling of cytokines with OVAglu was performed by incubation with stirring at 4° C. with an equimolar amount of target protein (human TGF-β1) at pH 8.5 in 0.1M carbonate buffer to deprotonate amino groups of the cytokine and allow their reaction with free glutaraldehyde components. After a 6-12 h incubation, a tenfold molar excess of PADRE peptide (aKXVAAWTLKAAC) (Alexander, J. et al (1994) Immunity 1:751-761) was added, and the mixture was incubated further overnight before dialysis against 0.1 M glycine buffer, pH 5.8.

Immunizations

Immunizations were performed by four to five biweekly s.c. injections into the footpads of 2-5 μg complexes emulsified in GERBU100 adjuvant, according to the instructions of the supplier (GERBU Biochemicals, Gaiberg, Germany). Mice were bled 2 weeks after the last boost. After a 2-6 week rest, a combined i.v. and i.p. booster with 2-5 μg complexes was given for mAb production.

Example 2

Binding of Isolated TGF-Beta Antibodies is Specific for TGF-Beta-1

Figure 3:
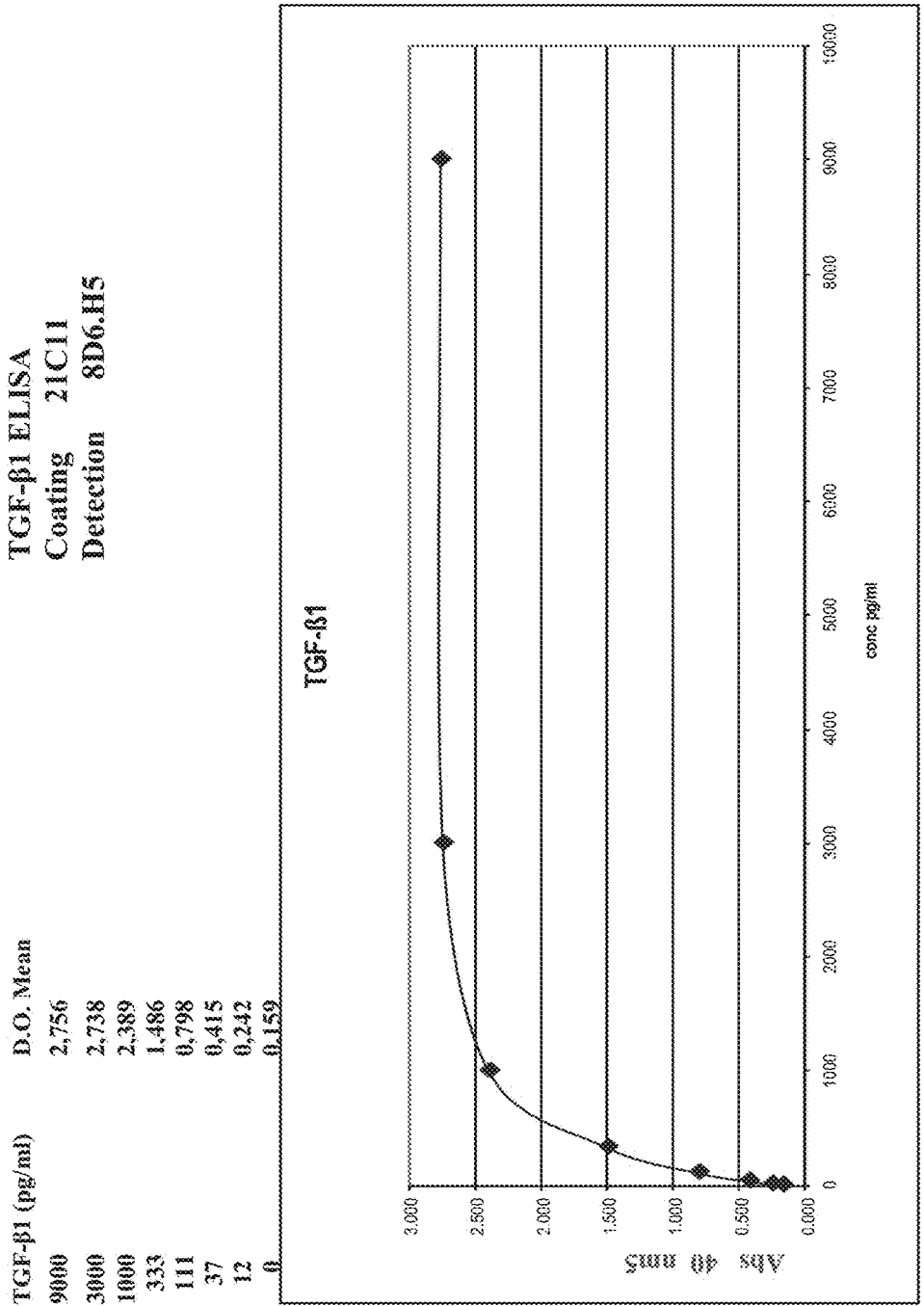
FIG. 3 provides data for detection of human TGF-beta1 by ELISA. Concentration of TGF-beta1 in ng/ml is graphed versus absorbance at 40 mm$^2$. Antibody 21C11 was used to coat ELISA plates, TGF-beta1 was detected using antibody 8D6.H5.

Isolated anti-TGF-beta antibodies generated by the protocol above were screened for binding ability to different TGF-beta isoforms. MAXISORB immunoplates were coated overnight at 4° C. with human TGF-beta-1, TGF-beta-2, or TGF-beta-3 (20-200 ng/ml in 50 mM glycine buffer, pH 9) or coated first with NEUTRAVIDIN at 2 ug/ml in PBS, followed by biotinylated antigens (100 ng/ml). Contrary to 1D11.16 (also denoted as 1D11) mouse monoclonal anti-TGF-beta antibody, an established reference anti-TGF-β antibody which recognizes TGF-β1, TGF-β2 and TGF-β3 (Dasch J R et al (1989) J Immunol 142:1536-1541), all the antibodies isolated, MTGF-beta-1.4C3.7, MTGF-beta1.8D6, MTGF-beta-1.19D8, MTGF-beta-1.4A11, MTGF-beta-1.19H11, MTGF-beta-1.21C11, MTGF-beta1.13A1 and MTGF-beta 1.4G9, bind only to TGF-beta-1 (FIG. 2). Detection of human TGF-beta-1 by sandwich ELISA is best achieved by using antibody 21C11, which is coated on an immunoabsorbent plate, to capture TGF-β1. TGF-β1 is then detected with antibody 8D6.H5 (FIG. 3).

Antibody Screening by ELISA.

Antibodies specific for the immunizing cytokine TGF-β1 were tested by ELISA on MAXISORB immunoplates (Nunc, Roskild, Denmark), coated overnight at 4° C. with the target antigen, e.g. TGF-β1 (20-200 ng/ml in 50 mM glycine buffer, pH 9), or coated first with NEUTRAVIDIN (Pierce Biotechnology, Rockford, Ill., USA) at 2 g/ml in PBS, followed by biotinylated antigens (100 ng/ml). After plate saturation with 1% BSA, sera were processed as described (Uyttenhove C et al (2006) Eur J Immunol 26:2868-2874).

Example 3

Neutralization of TGF-Beta-1 Activity

The TGF-β1 antibodies were tested for neutralizing activity by evaluating TGF-β1 mediated induction of the downstream gene PAI-1 in a luciferase assay in cells. MTGF-beta1.4C3.7, MTGF-beta1.4G9.1, MTGF-beta1.19D8 and MTGF-beta1.13A1 neutralize either human or mouse TGF-beta-1 activity. Antibodies MTGF-beta1.8D6, MTGF-beta1.4A11, MTGF-beta1.19H11 and MTGF-beta1.21C11 did not demonstrate TGF-beta1 activity neutralization in this assay (data not shown). Neutralization of TGF-beta-1 activity was demonstrated by evaluating loss of TGF-beta-mediated induction of downstream genes using methods described by Abe M et al. (Anal Biochem 1994 Feb. 1; 216(2):276-84). The expression of the PAI-1 gene was used to monitor TGF-beta activity.

Transfected mink lung epithelial cell line (TMLECs) were stably transfected with a truncated PAI-1 promoter fused to the firefly luciferase reporter gene. 500 pg/ml human TGF-beta-1 was incubated with serial serum dilutions of isolated TGFb1 antibody retrieved from mice serum for 4 h at 37° before transfer to an equal volume of culture medium (DMEM+10% FCS) where 50,000 TMLEC cells had been seeded 4 h earlier. After further 24 h incubation, luciferase activity was measured with the BRITELITE kit from Perkin-Elmer and luminescence was measured in a TOPCOUNT NXT from Perkin Elmer. Inhibitory serum titers are defined as the serum dilutions giving 50% inhibition of cytokine biological activities. Statistical significance (*$P<0.05$; $P<0.01$; *$P<0.001$) was calculated by Mann-Whitney or Student's t test as indicated.

Figure 4:
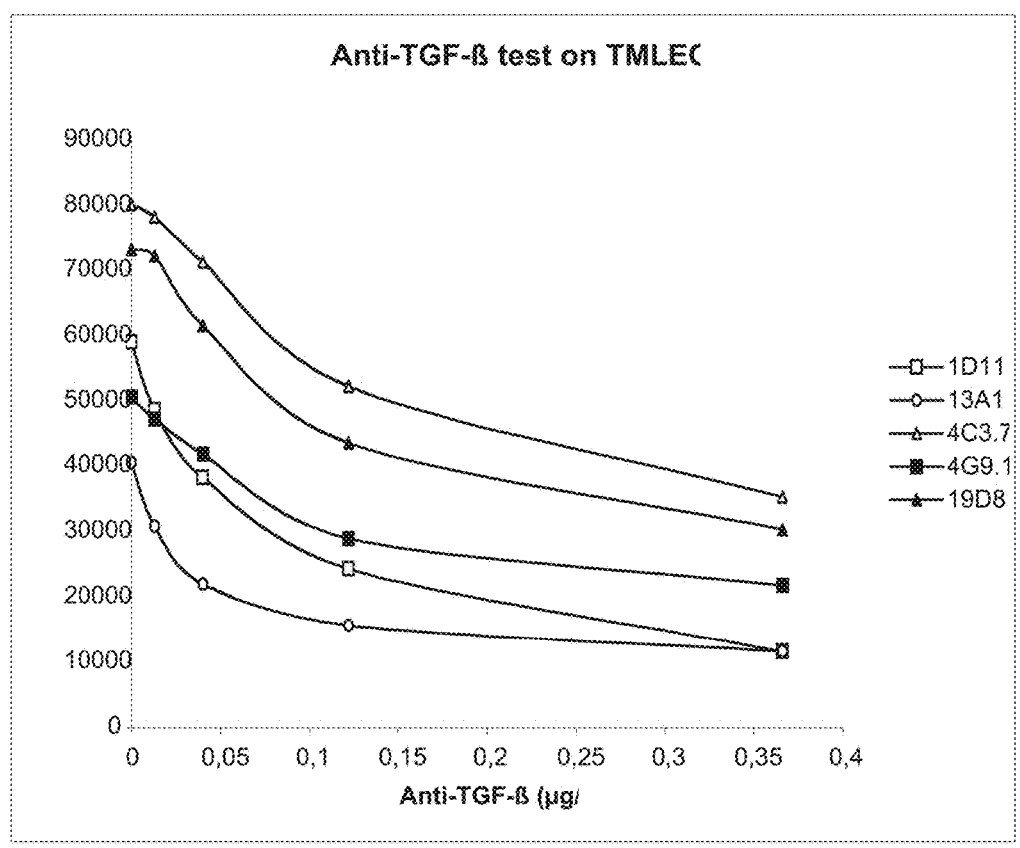
FIG. 4 shows neutralization of human TGF-beta1 in TMLEC cells, as assessed by expression of TGF-beta induced downstream gene PAI-1, from a PAI-1 luciferase construct. Neutralization by antibodies 1D11, 13A1, 4C3.7, 4G9.1 and 19D8 is shown.

In the presence of TGF-beta-1 antibodies in mouse serum, TGF-beta-mediated induction of PAI-1 promoter is reduced in a dose dependent manner. Inhibitory serum titers ranged from $10^3$ to $10^4$. In particular antibody 13A1 is very potent at inhibiting TGF-beta-1 bioactivity (FIG. 4). The data indicates that here appears to be a trend in improvement of 13A1 over prior art antibody 1D11.16 (1D11) in neutralizing TGF-beta-1.

Figure 5:
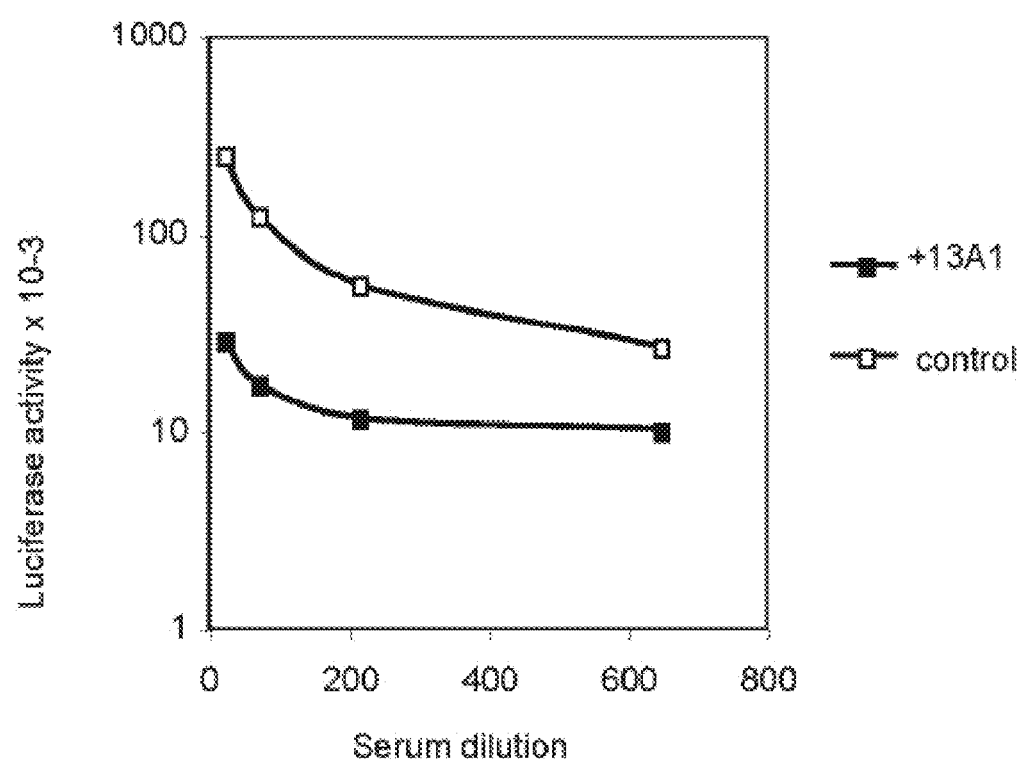
FIG. 5 shows antibody 13A1 inhibition of mouse TGF-beta1 (mTGF-β1) in vivo.

Antibody 13A1 also binds to TGF-β1 in vivo which results in removal of TGF-beta activity from mouse serum (FIG. 5). This was shown in studies in which FVB mice were treated with 13A1 (500 µg) and sera were collected 6 h later for testing, after acid treatment, for TGF-beta mediated induction of luciferase activity in TMLEC cells. To evaluate TGF-beta activity, sera were incubated with 0.16 M HCL for 10 min and neutralized with NaOH. This acid treatment is required to liberate active TGF-beta and thereby permit its interaction with TGF-beta receptor on the responder cell. It should also dissociate TGF-beta from any bound antibody and denature it. The fact that in vivo treatment with 13A1 abolished TGF-beta serum activity therefore suggests that 13A1 prompted elimination of TGF-beta from the blood because it is unlikely that remaining 13A1 could have resisted exposure of such strong acid.

Example 4

Graft Versus Host Disease

It has been shown that neutralization of TGF-beta after stem cell transplantation significantly increased the severity of acute Graft Versus Host Disease (GVHD) (Banovic T et al (2005) Blood 106(6):2206-2214). Thus, neutralizing activity of 13A1 in vivo was tested in a GVHD model. Graft-versus-host disease (GVHD) occurs in transplantation when immunocompetent donor cells are transferred into recipients or hosts that are incapable of rejecting the donor cells due to immune tolerance, host immature immune system or immune deficiency. A graft versus host reaction results following donor naïve T cells responding to allogeneic stimulators that cause differentiation into effector cells. The systemic effects of this initial donor anti-host reaction can result in multi-organ failure.

Murine GVHD models are used to understand transplantation immunobiology. Specifically, induction of GVHD in unirradiated immunocompetent adult F1 host mice was used to evaluate 13A1 neutralizing activity against TGF-β1. Spleen cells ($70 \times 10^6$) from parental strain C57BL/6 donors were injected intraperitoneally into unirradiated immunecompetent adult C57BL/6×DBA/2 on day 0 and day 6. The donor differs from the recipient at both class I and class II major histocompatibility (MHC) loci. In the F1 host, parental donor T cells expand and produce cytotoxic effectors, resulting in the elimination of the semiallogeneic host lymphohematopoietic system. Subsequently, the donor/host chimera is repopulated by donor cells derived from stem cells in the original splenic inoculum. A severe deficiency in both T and B cell function is observed for several weeks.

Figure 6A:
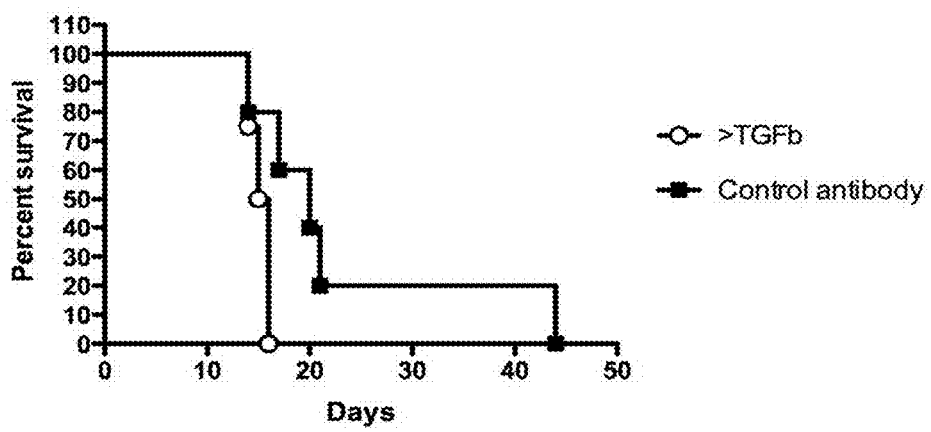
FIGS. 6A and 6B shows exacerbation of GVHD in animals treated with TGF-β1 antibody 13A1. (A) graph of percent survival in animals over 50 days. (B) graph of weight change (%) over 50 days. In each graph TGF-beta1 antibody treated animal data is compared versus animals administered IgG1 isotype control antibody.
Figure 6B:
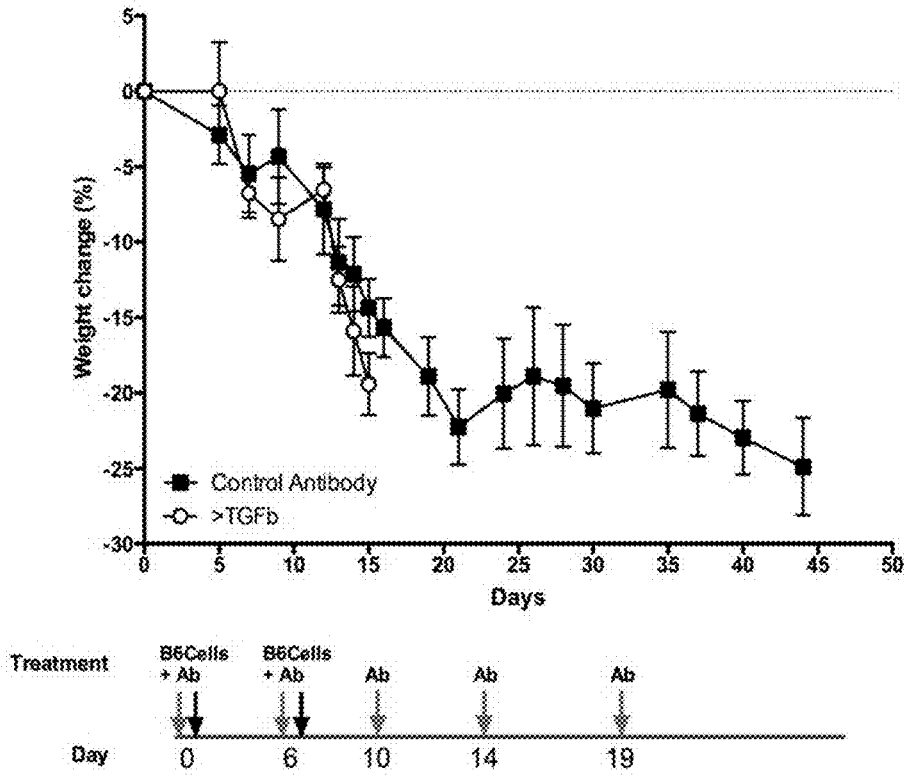

It is predicted that if immune suppression is dampened by 13A1-mediated neutralizing antibody to TGF-β1, then GVHD is exacerbated. To evaluate 13A1 neutralization activity during GVHD, antibodies to TGF-beta1 13A1 (0.5 mg) or IgG1 isotype control Ab (0.5 mg) were administered intraperitoneally at day 0, 5, 10, 14, and 19. Two treatment arms were used to determine the effect of blocking TGF-β1. In one arm, five mice received IgG1 isotype control Ab. In the second arm, 4 mice received 13A1 antibodies. GVHD response was assessed by monitoring survival (FIG. 6A) and weight loss (FIG. 6B) between treatment groups. Addition of 13A1 antibody exacerbated GVHD. Although weight loss is comparable in both treatment conditions, mice receiving TGF-beta neutralizing 13A1 antibodies died approximately at day 15 while 80% of the mice in the control group remained alive at this time.

Example 5

In Vivo Evaluation of TGF-β1 Specific Antibody

In human cancers, accumulating data shows that regulatory T-cells, CD4+FOXP3+ Tregs (Treg), are present in local tumor sites. Sato et al has demonstrated that the ratio of CD8+ T cells to CD4+CD25+FOXP3+ Tregs is an important prognostic indicator, with a low ratio associated with a poor outcome in ovarian cancer patients. This indicates the essential role of Treg in contributing to non-protective anti-tumor immune responses (Sato, E et al (2005) PNAS 102(51): 18538-18543). The cytokine TGFβ1 induces the conversion of T-cells to Tregs. Through Treg conversion and inhibition of T-cell activation, TGFβ1 also promotes tumor invasion and the progression of metastatic disease in later stages of tumorigenesis. Since TGFβ1-induced T-reg conversion contributes to attenuation of immune responses and poor prognosis, TGFβ inhibitor may contribute to reduction in the number of T-reg cells, enhancement of anti-tumor immune responses and reduction in tumor progression.

Earlier work in mouse tumor models showed that treatment with antagonist pan TGFβ neutralizing antibodies resulted in stimulation of tumor antigen-specific T-cell activity along with decreased Treg populations. These antibodies were determined to reduce tumor infiltrating FoxP3+ regulatory T-cell populations, indicating that the pan-TGFβ neutralizing antibodies blocked the conversion of T-cells to regulatory T-cells and reduced tumor metastasis (Liu V C et al (2007) J Immunol 178(5): 2883-92).

There are multiple forms of TGFβ therefore selectively blocking TGFβ1 is necessary in order to achieve the full therapeutic potential of blocking TGFβ1-induced immune suppression for the treatment of cancer. We evaluate blocking TGFβ1 specifically with neutralizing antibodies that target only TGFβ1 and fail to bind to other forms of TGFβ. The inhibitory activity of anti-TGFβ1 on tumor growth and metastasis is tested in mouse models. The models are utilized for investigating tumor protection, enhancement and immunosuppression.

Neutralizing antibodies to TGFβ1 are tested in established tumors in subcutaneous models or metastasis models in order to determine anti-TGFβ1 antitumor activity against primary and metastatic tumors. Tumors are allowed to grow to approximately 200 mm in size, and then mice randomized into treatment groups. In lung metastasis models, mice are injected intravenously with tumor cells via the tail vein. Anti-TGFβ1 antibody is tested in a mouse that receives i.p. or iv administered anti-TGFβ1 antibody over a range of dosages with 2-10 fold differences comparable to dosages used in GVHD model (0.5 mg). Mice in control groups receive an equal volume of saline or normal IgG1 solution. Treatment of the animals is continued for the duration of the experiment. Tumor volumes are calculated using any standard methods well known in the art.

Tumor volume data is analyzed to determine the significant differences in tumor sizes among treatments, time points, and treatment-time interactions. A P value of less than 0.05 is considered to be statistically significant. Anti-TGFβ1 antibody significantly inhibits primary tumor growth and spontaneous pulmonary metastasis in a tumor model.

The inhibitory activity of anti-mouse TGFβ1 against T-cell conversion to CD4/CD25/Foxp3 Treg cells is evaluated in tumor models. Briefly, purified naïve CD4+ cells isolated from tumor samples from anti-TGFβ-1 antibody or IgG1 control groups are activated by stimulation using methods well known in the art. The inhibitory effect of anti-TGFβ1 antibody on T-cell conversion to Treg in tumor-bearing mice is determined by FACS analysis to evaluate the changes in CD4/CD25/Foxp3 population after treatment of mice with anti-TGFβ1 antibody. Anti-mouse TGFβ1 antibody significantly decreases the number CD4/CD25/Foxp3 Treg cells in treated mice bearing tumors as compared to IgG1 control. These results indicate that anti-TGFβ1 antibodies may control the CD4/CD25/Foxp3 population by inhibition or/and depletion of Treg.

The contribution of the inhibitory activity of anti-TGFβ1 antibody to immune enhancement is evaluated by assessing tumor-associated T cells derived from tumor biopsy samples for TCR activation. Briefly, purified naïve CD4+ cells isolated from tumor samples from anti-TGFβ-1 antibody or IgG1 control groups are activated by stimulation of T-cells using methods well known in the art. The cells are evaluated for enhanced T-cell activity by looking for loss of T-reg-induced T-cell anergy, including monitoring the production of cytokines and activation markers by methods well known in the art (Broderick L. et al (2006) J Immunol 177:3082-3088). Anti-TGFβ1 antibody enhances T-cell activation compared to control IgG1 treated cells.

Human CTLA-4 mAb has been found to elicit objective and durable clinical responses in a subset of melanoma patients. Previous studies have demonstrated that blockade of CTLA-4 action by monoclonal antibodies enhances effector T cell responses and induces T cell mediated tumor rejection in mouse models (Fong L et al (2008) J Clin Oncol 26:5275-5283). However, the effectiveness of such immuno therapy can be blunted by Treg. CLTA-4 blockade induces an increase in the number of Tregs as well as the number of CD8+ T cells. Considering the importance of Treg in suppression of anti-tumor immune responses, controlling Tregs is an important and clinically relevant goal. We have therefore sought to augment immune responses by combinational modulation of regulatory molecules including IDO, TDO, α-galactosyl ceramide and analogs thereof such as IMM47 Lag3, iCOS, GITR, GITR ligand, CTLA-4, PD1, PD1 ligand, OX40 and OX40 ligand. OX40 agonists are listed in published patent application US2012/0141465 based on U.S. Ser. No. 11/867,621. Garison K et al reported anti-OX40 mutually enhanced anti-TGFβ1 to elicit a potent anti-tumor effect against established primary tumors (Garrison K et al (2012) Cancer Immunol Immunother April; 61 (4):511-21). Additional immunmodulators are small molecules, antagonist antibodies or agonist antibodies targeting the applicable immune modulators include IDO, TDO, Toll like receptor family or iCOS, CTLA-4, PD1, PD1 ligand, OX40 and OX40 ligand, interleukins, tumor necrosis factor (TNF) or other growth factors, colony stimulating factors, T cell modulators including modulators of CD8+ T cells, cytokines which stimulate the immune response or reduction or elimination of cancer cells or tumors.

Additionally, the anti-TGFβ1 antibodies of the present invention may be administered alone, or in combination with an anti-neoplastic agent other than anti-TGFβ1 antibodies, radiation, other TGFβRII antagonists, TGFβ antagonists, antibodies to other targets, and small molecules. The administration of the antibodies with other antibodies and/or treatments may occur simultaneously, or separately, via the same or different route, at the same or different times.

Given the clinical limitations reported for therapeutic cancer vaccines strategies, combining the inhibition of tumor-derived TGFβ1 and Treg mediated immuno suppression with a targeted vaccine or immunogene strategy may provide the necessary synergy to overcome tumor immune-evasion mechanisms. We have therefore sought to augment immune responses by combining anti-TGFβ1 antibodies with Cancer Testis antigens, including Cancer Testis antigen MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, MAGE-A13, GAGE-1, GAGE-2, GAGE-3, GAGE-4, GAGE-5, GAGE-6, GAGE-7, GAGE-8, BAGE-1, RAGE-1, LB33/MUM-1, PRAME, NAG, MAGE-Xp2 (MAGE-B2), MAGE-Xp3 (MAGE-B3), MAGE-Xp4 (MAGE-B4), tyrosinase, brain glycogen phosphorylase, Melan-A, MAGE-C1, MAGE-C2, NY-ESO-1, LAGE-1, SSX-1, SSX-2(HOM-MEL-40), SSX-1, SSX-4, SSX-5, SCP-1 and CT-7. For example, antigenic peptides characteristic of tumors include those listed in published PCT application WO00/20581 (PCT/US99/21230), in published US application US2012/0328660 based on U.S. Ser. No. 13/484,884 and 61/493,164 and in Sabbatini P J et al (2012) Clin Cancer Res 18, 6497.

Example 6

Binding Characteristics of TGF-β1 Antibodies

Figure 7:
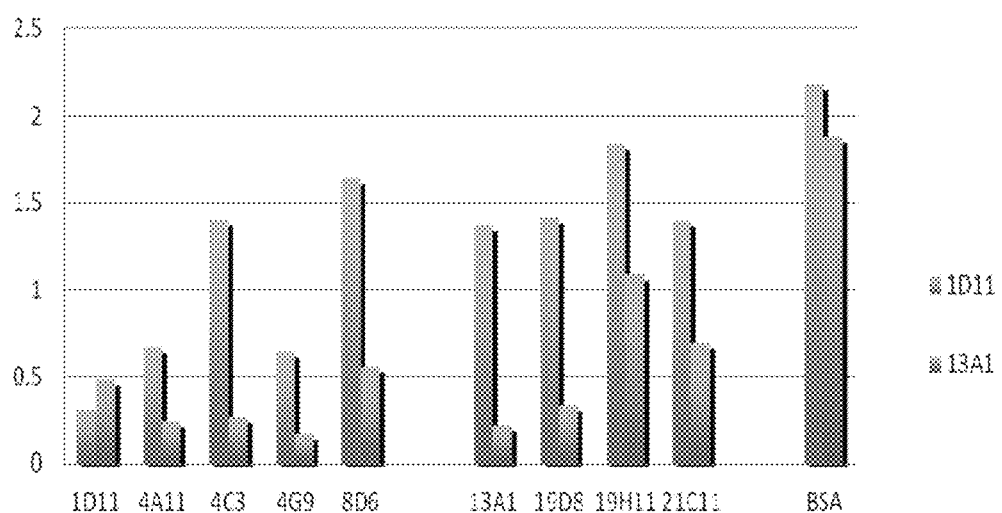
FIG. 7 depicts TGF-β1 antibody binding characteristics as assessed in competitive binding assays with antibody 1D11 and antibody 13A1.

The relative binding characteristics of the isolated TGF-β1 antibodies were compared in competition binding experiments versus either 1D11, which binds all TGF-β forms) and TGF-β1 specific antibody 13A1. In each instance, biotinylated human TGF-β1 (20 ng/ml) was incubated overnight with monoclonal TGF-β1 antibody 13A1 (20 μg/ml) or pan antibody 1D11 or BSA. After overnight pre-incubation period, the antibody binding mixtures were transferred to plates coated with antibodies 1D11, 4A11, 4C3, 4G9, 8D6, 13A1, 19D8, 19H11, 21C11 or BSA. The plates were incubated for 2 h. After 2 h at 37°, streptavidin-HRP was added for 1 h. If biotinylated TGF-β1 binds to the plate, the coated Abs react with a site on TGF-β1 that was not masked during pre-incubation with either 1D11 or 13A1. The results are provided in FIG. 7.

This invention may be embodied in other forms or carried out in other ways without departing from the spirit or essential characteristics thereof. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

---

What is claimed is:

1. An isolated nucleic acid which comprises a sequence encoding an antibody or fragment thereof which recognizes human and mouse transforming growth factor beta 1 (TGF-β1) and does not react with TGF-β2 and does not react with TGF-β3, wherein the antibody or fragment neutralizes activity of TGF-β1, and is an antibody or fragment comprising a heavy chain variable region comprising CDR domain sequences CDR1 GYTFTNYW (SEQ ID NO: 11), CDR2 IYPGNSDT (SEQ ID NO: 12) and CDR3 EDSRSLYYN-GWDYFDY (SEQ ID NO: 5) or comprising CDR domain sequences CDR1 GYTFTNYWMH (SEQ ID NO: 3), CDR2 TIYPGNSDTN (SEQ ID NO: 4) and CDR3 EDSRSLYYN-GWDYFDY (SEQ ID NO: 5), and a light chain variable region comprising CDR domain sequences CDR1 ESVD-NYGISF (SEQ ID NO: 6), CDR2 YAAS (SEQ ID NO: 7) and CDR3 QQSKEVPRT (SEQ ID NO: 8).

2. The nucleic acid of claim 1 which encodes an antibody or antibody fragment comprising a heavy chain variable region comprising CDR domain sequences CDR1 GYTFT-NYW (SEQ ID NO: 11), CDR2 IYPGNSDT (SEQ ID NO: 12) and CDR3 EDSRSLYYNGWDYFDY (SEQ ID NO: 5) and a light chain variable region comprising CDR domain sequences CDR1 ESVDNYGISF (SEQ ID NO: 6), CDR2 YAAS (SEQ ID NO: 7) and CDR3 QQSKEVPRT (SEQ ID NO: 8).

3. The nucleic acid of claim 1 which encodes an antibody or antibody fragment comprising a heavy chain variable region comprising CDR domain sequences CDR1 GYTFT-NYWMH (SEQ ID NO: 3), CDR2 TIYPGNSDTN (SEQ ID NO: 4) and CDR3 EDSRSLYYNGWDYFDY (SEQ ID NO: 5) and a light chain variable region comprising CDR domain sequences CDR1 ESVDNYGISF (SEQ ID NO: 6), CDR2 YAAS (SEQ ID NO: 7) and CDR3 QQSKEVPRT (SEQ ID NO: 8).

4. The nucleic acid of claim 1 which encodes an antibody or antibody fragment comprising a heavy chain variable region amino acid sequence selected from the amino acid sequence SEQ ID NO: 1, or variants thereof having at least 90% amino acid identity to SEQ ID NO:1.

5. The nucleic acid of claim 1 or 4 which encodes an antibody or antibody fragment comprising a light chain variable region comprising an amino acid sequence selected from the amino acid sequence as set out in SEQ ID NO: 2, or variants thereof having at least 90% amino acid identity to SEQ ID NO:2.

6. The nucleic acid of claim 1 which comprises DNA.

7. A recombinant DNA molecule comprising the sequence of claim 1.

8. The recombinant DNA molecule of claim 7, wherein said sequence is operatively linked to an expression control sequence.

9. A unicellular host transformed with a recombinant DNA molecule of claim 7 or 8.

10. A vector which comprises the recombinant DNA molecule of claim 7 or 8.

11. An isolated host vector system for the production of an antibody or fragment thereof which comprises the vector of claim 10 in a suitable host cell.

12. A method of preparing an antibody or fragment thereof which recognizes human and mouse transforming growth factor beta 1 (TGF-β1) and does not react with TGF-β2 and does not react with TGF-β3, wherein the antibody or fragment neutralizes activity of TGF-β1, which comprises expressing the nucleic add of claim 1 or any one of claims 2-4 under conditions to bring about expression of said antibody or fragment, and recovering the antibody or fragment.

* * * * *